(12) United States Patent
Lin et al.

(10) Patent No.: US 7,576,239 B2
(45) Date of Patent: Aug. 18, 2009

(54) SUBSTITUTED AMIDES

(75) Inventors: Linus S. Lin, Westfield, NJ (US);
William K. Hagmann, Westfield, NJ (US); Sanjeev Kumar, Manalapan, NJ (US); Wenji Yin, Edison, NJ (US);
George Doss, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 12/008,728

(22) Filed: Jan. 14, 2008

(65) Prior Publication Data

US 2008/0194645 A1 Aug. 14, 2008

Related U.S. Application Data

(62) Division of application No. 10/538,395, filed as application No. PCT/US03/40040 on Dec. 15, 2003, now Pat. No. 7,348,456.

(60) Provisional application No. 60/435,436, filed on Dec. 19, 2002.

(51) Int. Cl.
*C07C 233/05* (2006.01)
*C07D 213/02* (2006.01)
*A61K 31/44* (2006.01)

(52) U.S. Cl. .................. 564/175; 564/123; 564/161; 564/168; 514/345

(58) Field of Classification Search .................. None
See application file for complete search history.

(56) References Cited

U.S. PATENT DOCUMENTS

| | | | |
|---|---|---|---|
| 4,360,519 A | 11/1982 | White et al. | |
| 5,281,611 A * | 1/1994 | Sawyer et al. | ............... 514/297 |
| 6,344,474 B1 | 2/2002 | Maruani et al. | |
| 6,359,175 B1 | 3/2002 | Philippe et al. | |
| 7,348,456 B2 * | 3/2008 | Lin et al. | ............... 564/123 |
| 2003/0114495 A1 | 6/2003 | Finke et al. | |
| 2004/0058820 A1 | 3/2004 | Hagmann et al. | |
| 2004/0224962 A1 | 11/2004 | Coe et al. | |
| 2004/0224963 A1 | 11/2004 | Coe et al. | |
| 2004/0248956 A1 | 12/2004 | Hagmann et al. | |
| 2005/0137159 A1 | 6/2005 | Bab et al. | |
| 2005/0154202 A1 | 7/2005 | Hagmann et al. | |
| 2005/0171161 A1 | 8/2005 | Fong et al. | |
| 2005/0182103 A1 | 8/2005 | Finke et al. | |
| 2006/0106071 A1 | 5/2006 | Lin et al. | |

FOREIGN PATENT DOCUMENTS

| | | |
|---|---|---|
| GB | 899556 | 6/1962 |
| GB | 1172346 | 11/1969 |
| WO | WO 98/33765 | 8/1998 |
| WO | WO 98/56754 | 12/1998 |
| WO | WO 01/09120 | 2/2001 |
| WO | WO 01/58450 | 8/2001 |
| WO | WO 03/007887 | 1/2003 |
| WO | WO 03/009005 | 1/2003 |
| WO | WO 03/063781 | 8/2003 |
| WO | WO 03/075660 | 9/2003 |
| WO | WO 03/077847 | 9/2003 |
| WO | WO 03/082256 | 10/2003 |
| WO | WO 03/082833 | 10/2003 |
| WO | WO 03/086288 | 10/2003 |
| WO | WO 03/087037 | 10/2003 |
| WO | WO 2004/012671 | 2/2004 |
| WO | WO 2004/029204 | 4/2004 |
| WO | WO 2004/048317 | 6/2004 |
| WO | WO2004/058145 | 7/2004 |
| WO | WO 2005/000301 | 1/2005 |
| WO | WO 2005/000809 | 1/2005 |
| WO | WO 2005/009479 | 2/2005 |
| WO | WO 2005/020988 | 3/2005 |
| WO | WO 2005/020992 | 3/2005 |
| WO | WO 2005/027837 | 3/2005 |
| WO | WO 2005/039550 | 5/2005 |
| WO | WO 2005/043327 | 5/2005 |

OTHER PUBLICATIONS

Finkelstein et al. Journal of Medicinal Chemistry, 1971, 14, p. 584-588.*
Lange et al., Drug Discovery Today, vol. 10 (2005), pp. 693-702, "Medicinal chemistry strategies to CB1 cannabinoid receptor antagonists".
Petitet et al., Emerging Drugs, vol. 3 (1998), pp. 39-53, "The therapeutic applications of cannabinoid agonists and antagonists".
Di Marzo et al., Emerging Therapeutic Targets, vol. 5 (2001), pp. 241-265, "Endocannabinoids Part I: Molecular basis fo endocannabinoid formation, action and inactivation and development of selectie inhibitors".

(Continued)

*Primary Examiner*—Paul A Zucker
*Assistant Examiner*—Yevegeny Valenrod
(74) *Attorney, Agent, or Firm*—Baerbel R. Brown; Catherine D. Fitch

(57) ABSTRACT

Novel compounds of the structural formula (I) are antagonists and/or inverse agonists of the Cannabinoid-1 (CB1) receptor and are useful in the treatment, prevention and suppression of diseases mediated by the CB1 receptor. The compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, the treatment of obesity or eating disorders, as well as the treatment of asthma, constipation, chronic intestinal pseudo-obstruction, and cirrhosis of the liver.

12 Claims, No Drawings

OTHER PUBLICATIONS

Goya et al., Exp. Opin. Ther. Patents, vol. 10 (2000), pp. 1529-1538, "Recent advances in cannabinoid receptor agonists and antagonists".

Adam et al., Exp. Opin. Ther. Patents, vol. 12 2002), pp. 1475-1489, "Recent advances in the cannabinoids".

Barth, Exp. Opin. Ther. Patents, vol. 8 (1998), pp. 301-313, "Cannabinoid receptor agonists and antagonists".

Ito et al., Chem. Pharm. Bull., vol. 20 (1972), pp. 1762-1767, "Catalytic hydrogenation of tetrahydro-4H-1,3-oxazin-4-ones and 4-oxazolidinones".

Ishiwata et al., Yakugaku Zashi, vol. 71 (1951), pp. 1272-1274, "Studies on the syntheses of isoquinoline derivatives".

Grundy et al., Exp. Opin. Investig. Drugs, vol. 11 (2002), pp. 1365-1374, "The therapeutic potential of the cannabinoids in neuroprotection".

Pines et al., J. Med. Chem., vol. 10 (1967), pp. 725-728, "The stereochemistry of 2,3-diphenyl-1-methylpropylamine".

Schultz et al., J. Med. Chem., vol. 10 (1967), pp. 717-724, "Maleamic acids that affect plasma cholesterol and penicillin excretion".

Le Foll et al., J. Pharmacol. Exp. Ther., vol. 312 (2005), pp. 875-883, "Cannabinoid CB1 receptor antagonists as promising new medications for drug dependence".

Konosu et al., Chem. Pharm. Bull., vol. 39 (1991), pp. 2581-2589, "Triazole antifungals . . .".

Novak et al., Pestic. Sci., vol. 49 (1997), pp. 85-89, "Preparation of novel hexythiazox anaogues".

Canonica et al., Gazzetta Chimica Italiana, vol. 84 (1954), pp. 175-186, "The action of Grignard reagents on α-diazo ketones".

Database HCAPLUS, Hagmann et al., XP002513691, No. 2003:796415 (2003), "Preparation of spirocyclic carboxamides as cannabinoid receptor modulators".

Database HCAPLUS, Hagmann et al., XP002513692, No. 2003:837028 (2003), "Preparation of substituted arylamides as cannabinoid-1 receptor antagonists and/or inverse agonists for use as psychotropic drugs".

* cited by examiner

SUBSTITUTED AMIDES

CROSS-REFERENCE TO RELATED APPLICATIONS

This application is a divisional application of U.S. Ser. No. 10/538,395, filed Jun. 9, 2005, now U.S. Pat. No. 7,348,456 which is a U.S. National Phase application under 35 U.S.C. §371 of PCT Application No. PCT/US2003/040040, filed Dec. 15, 2003, which claims priority under 35 U.S.C. §119 from U.S. Provisional Application No. 60/435,436, filed Dec. 19, 2002.

BACKGROUND OF THE INVENTION

Marijuana (*Cannabis sativa L.*) and its derivatives have been used for centuries for medicinal and recreational purposes. A major active ingredient in marijuana and hashish has been determined to be $\Delta^9$-tetrahydrocannabinol ($\Delta^9$-THC). Detailed research has revealed that the biological action of $\Delta^9$-THC and other members of the cannabinoid family occurs through two G-protein coupled receptors termed CB1 and CB2. The CB1 receptor is primarily found in the central and peripheral nervous systems and to a lesser extent in several peripheral organs. The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to $\Delta^9$-THC, including sedation, hypothermia, intestinal immobility, antinociception, analgesia, catalepsy, anti-emesis, and appetite stimulation.

The genes for the respective cannabinoid receptors have each been disrupted in mice. The CB1$^{-/-}$ receptor knockout mice appeared normal and fertile. They were resistant to the effects of $\Delta^9$-THC and demonstrated a strong reduction in the reinforcing properties of morphine and the severity of withdrawal syndrome. They also demonstrated reduced motor activity and hypoalgesia. The CB2$^{-/-}$ receptor knockout mice were also healthy and fertile. They were not resistant to the central nervous system mediated effects of administered $\Delta^9$-THC. There were some effects on immune cell activation, reinforcing the role for the CB2 receptor in immune system functions.

Excessive exposure to $\Delta^9$-THC can lead to overeating, psychosis, hypothermia, memory loss, and sedation. Specific synthetic ligands for the cannabinoid receptors have been developed and have aided in the characterization of the cannabinoid receptors: CP55,940 (J. Pharmacol. Exp. Ther. 1988, 247, 1046-1051); WIN55212-2 (J. Pharmacol. Exp. Ther. 1993, 264, 1352-1363); SR141716A (FEBS Lett. 1994, 350, 240-244; Life Sci. 1995, 56, 1941-1947); and SR144528 (J. Pharmacol. Exp. Ther. 1999, 288, 582-589). The pharmacology and therapeutic potential for cannabinoid receptor ligands has been reviewed (Exp. Opin. Ther. Patents 1998, 8, 301-313; Ann. Rep. Med. Chem., A. Doherty, Ed.; Academic Press, NY 1999, Vol. 34, 199-208; Exp. Opin. Ther. Patents 2000, 10, 1529-1538; Trends in Pharma. Sci. 2000, 21, 218-224). There is at least one CB1 modulator characterized as an inverse agonist or an antagonist, N-(1-piperidinyl)-5-(4-chlorophenyl)-1-(2,4-dichlorophenyl)-4-methylpyrazole-3-carboxamide (SR141716A), in clinical trials for treatment of eating disorders at this time. There still remains a need for potent low molecular weight CB1 modulators that have pharmacokinetic and pharmacodynamic properties suitable for use as human pharmaceuticals.

Treatment of asthma with CB1 receptor modulators (such as CB1 inverse agonists) is supported by the finding that presynaptic cannabinoid CB1 receptors mediate the inhibition of noradrenaline release (in the guinea pig lung) (Europ. J. of Pharmacology, 2001, 431 (2), 237-244).

Treatment of cirrhosis of the liver with CB1 receptor modulators is supported by the finding that a CB1 receptor modulator will reverse the low blood pressure observed in rats with carbon tetrachloride-induced liver cirrhosis and will lower the elevated mesenteric blood flow and portal vein pressure (Nature Medicine, 2001, 7 (7), 827-832).

U.S. Pat. Nos. 5,624,941 and 6,028,084, PCT Application Nos. WO98/31227, WO98/41519, WO98/43636, WO98/43635 and WO 02/076949, and EPO Application No. EP-658546 disclose substituted pyrazoles having activity against the cannabinoid receptors.

PCT Application Nos. WO98/37061, WO00/10967, and WO00/10968 disclose diaryl ether sulfonamides having activity against the cannabinoid receptors.

PCT Application Nos. WO97/29079 and WO99/02499 disclose alkoxy-isoindolones and alkoxy-quinolones as having activity against the cannabinoid receptors.

U.S. Pat. No. 5,532,237 discloses N-benzoyl-indole derivatives having activity against the cannabinoid receptors.

U.S. Pat. Nos. 4,973,587, 5,013,837, 5,081,122, and 5,112,820, 5,292,736 disclose aminoalkylindole derivatives as having activity against the cannabinoid receptors.

PCT publication WO 01/58869 discloses pyrazoles, pyrroles and imidazole cannabinoid receptor modulatorsuseful for treating respiratory and non-respiratory leukocyte activation-associated disorders.

PCT publications WO 01/64632, 01/64633, and 01/64634 are directed to azetidine derivatives as cannabinoid antagonists.

Schultz, E. M, et al. *J. Med Chem.* 1967, 10, 717 and Pines, S. H. et al. *J. Med. Chem.* 1967, 10, 725 disclose maleamic acids affecting plasma cholesterol and penicillin excretion.

The compounds of the present invention are modulators of the Cannabinoid-1 (CB1) receptor and are useful in the treatment, prevention and suppression of diseases mediated by the Cannabinoid-1 (CB1) receptor. In particular, compounds of the present invention are antagonists or inverse agonists of the CB1 receptor. The invention is concerned with the use of these compounds to modulate the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of eating disorders by inhibiting excessive food intake and the resulting obesity and complications associated therewith. The compounds are also useful for the treatment of constipation and chronic intestinal pseudo-obstruction, as well as for the treatment of asthma, and cirrhosis of the liver.

SUMMARY OF THE INVENTION

The present invention is concerned with novel substituted amides of the general Formula I:

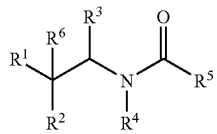

and pharmaceutically acceptable salts thereof which are antagonists and/or inverse agonists of the Cannabinoid-1 (CB1) receptor and are useful in the treatment, prevention and suppression of diseases mediated by the Cannabinoid-1 (CB1) receptor. The invention is concerned with the use of these novel compounds to selectively antagonize the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine, including smoking cessation. The compounds are also useful for the treatment of obesity or eating disorders associated with excessive food intake and complications associated therewith. The compounds are also useful for the treatment of constipation and chronic intestinal pseudo-obstruction. The compounds are also useful for the treatment of cirrhosis of the liver. The compounds are also useful for the treatment of asthma.

The present invention is also concerned with treatment of these conditions, and the use of compounds of the present invention for manufacture of a medicament useful in treating these conditions. The present invention is also concerned with treatment of these conditions through a combination of compounds of formula I and other currently available pharmaceuticals.

The invention is also concerned with novel compounds of structural formula I.

The invention is also concerned with pharmaceutical formulations comprising one of the compounds as an active ingredient.

The invention is further concerned with processes for preparing the compounds of this invention.

DETAILED DESCRIPTION OF THE INVENTION

The compounds used in the methods of the present invention are represented by the compound of structural formula I:

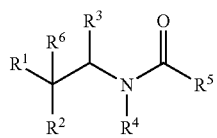

or a pharmaceutically acceptable salt thereof, wherein;
$R^1$ is selected from:
(1) aryl,
(2) aryl-$C_{1-4}$alkyl,
(3) heteroaryl,
(4) heteroaryl-$C_{1-4}$alkyl,
wherein each alkyl is optionally substituted with one to four substituents independently selected from $R^a$, and each aryl and heteroaryl are optionally substituted with one to four substituents independently selected from $R^b$;
$R^2$ is selected from:
(1) $C_{1-10}$alkyl,
(2) $C_{3-10}$cycloalkyl-$C_{1-4}$alkyl,
(3) cycloheteroalkyl,
(4) cycloheteroalkyl-$C_{1-4}$alkyl,
(5) aryl,
(6) aryl-$C_{1-4}$alkyl,
(7) heteroaryl, and
(8) heteroaryl-$C_{1-4}$alkyl,
wherein each alkyl is optionally substituted with one to four substituents independently selected from $R^a$, and each cycloalkyl, cycloheteroalkyl, aryl and heteroaryl is optionally substituted with one to four substituents independently selected from $R^b$;
$R^3$ is selected from:
(1) hydrogen, and
(2) $C_{1-4}$alkyl,
wherein each alkyl is optionally substituted with one to four substituents independently selected from $R^a$;
$R^4$ is selected from:
(1) hydrogen, and
(2) $C_{1-4}$alkyl,
wherein each alkyl is optionally substituted with one to four substituents independently selected from $R^a$;
$R^5$ is selected from:
(1) $C_{1-10}$alkyl,
(2) $C_{2-10}$alkenyl,
(3) $C_{3-10}$cycloalkyl,
(4) $C_{3-10}$cycloalkyl-$C_{1-10}$alkyl,
(5) cycloheteroalkyl-$C_{1-10}$alkyl,
(6) aryl-$C_{1-10}$alkyl,
(7) diaryl-$C_{1-10}$alkyl,
(8) aryl-$C_{2-10}$alkenyl,
(9) heteroaryl-$C_{1-10}$alkyl,
(10) —$OR^d$, and
(11) —$NR^cR^d$,
wherein alkyl, alkenyl, cycloalkyl, and cycloheteroalkyl are optionally substituted with one to four substituents independently selected from $R^a$ and cycloalkyl, cycloheteroalkyl, aryl and heteroaryl are optionally substituted with one to four substituents independently selected from $R^b$, provided that $R^5$ is not —CH=CH—COOH;
$R^6$ is selected from:
(1) $C_{1-4}$alkyl,
(2) $C_{2-4}$alkenyl,
(3) $C_{2-4}$alkynyl,
(4) —$OR^d$,
(5) halogen,
(6) —CN,
(7) —$NR^cR^d$,
wherein alkyl, alkenyl, and alkynyl are optionally substituted with one to four substituents independently selected from $R^a$
each $R^a$ is independently selected from:
(1) —$OR^d$,
(2) —$NR^cS(O)_mR^d$,
(3) halogen,
(4) —$S(O)_mR^d$,
(5) —$S(O)_mNR^cR^d$,
(6) —$NR^cR^d$, (7) —C(O)R$^d$,
(8) —CO$_2$R$^d$,
(9) —CN,
(10) —C(O)NR$^c$R$^d$,
(11) —NR$^c$C(O)R$^d$,
(12) —NR$^c$C(O)OR$^d$,
(13) —NR$^c$C(O)NR$^c$R$^d$,
(14) —CF$_3$,
(15) —OCF$_3$, and
(16) cycloheteroalkyl;

each R$^b$ is independently selected from:
(1) R$^a$,
(2) C$_{1-10}$alkyl,
(3) oxo,
(4) aryl,
(5) arylC$_{1-4}$alkyl,
(6) heteroaryl, and
(7) heteroarylC$_{1-4}$alkyl;

R$^c$ and R$^d$ are independently selected from:
(1) hydrogen,
(2) C$_{1-10}$alkyl,
(3) C$_{2-10}$alkenyl,
(4) cycloalkyl,
(5) cycloalkyl-C$_{1-10}$alkyl;
(6) cycloheteroalkyl,
(7) cycloheteroalkyl-C$_{1-10}$alkyl;
(8) aryl,
(9) heteroaryl,
(10) aryl-C$_{1-10}$alkyl, and
(11) heteroaryl-C$_{1-10}$alkyl, or R$^c$ and R$^d$ together with the atom(s) to which they are attached form a heterocyclic ring of 4 to 7 members containing 0-2 additional heteroatoms independently selected from oxygen, sulfur and N—R$^g$, each R$^c$ and R$^d$ may be unsubstituted or substituted with one to three substituents selected from R$^h$;

each R$^g$ is independently selected from
(1) C$_{1-10}$alkyl, and
(2) —C(O)R$^c$;

each R$^h$ is independently selected from:
(1) halogen,
(2) C$_{1-10}$alkyl,
(3) —O—C$_{1-4}$alkyl,
(4) —S(O)$_m$-C$_{1-4}$alkyl,
(5) —CN,
(6) —CF$_3$, and
(7) —OCF$_3$; and m is selected from 0, 1 and 2.

In one embodiment of the present invention, when R$^1$ is unsubstituted phenyl, R$^2$ is unsubstituted benzyl, R$^3$ is unsubstituted methyl, and R$^4$ is hydrogen, then R$^5$ is neither unsubstituted methyl nor unsubstituted phenyl; and when R$^1$ is unsubstituted benzyl, R$^2$ is unsubstituted phenyl, R$^3$ is unsubstituted methyl, and R$^4$ is hydrogen, then R$^5$ is neither unsubstituted methyl nor unsubstituted phenyl; and when R$^1$ is unsubstituted phenyl, R$^2$ is 4-methoxybenzyl, R$^3$ is methyl, R$^4$ is hydrogen, then R$^5$ is not 3,4,5,-trimethoxyphenyl; and when R$^1$ is 4-methoxybenzyl, R$^2$ is unsubstituted phenyl, R$^3$ is methyl, R$^4$ is hydrogen, then R$^5$ is not 3,4,5,-trimethoxyphenyl.

In another embodiment of the present invention, when R$^1$ is unsubstituted phenyl, R$^2$ is unsubstituted benzyl, R$^3$ is unsubstituted methyl, and R$^4$ is hydrogen, then R$^5$ is not unsubstituted methyl; and when R$^1$ is unsubstituted benzyl, R$^2$ is unsubstituted phenyl, R$^3$ is unsubstituted methyl, and R$^4$ is hydrogen, then R$^5$ is not unsubstituted methyl.

In one embodiment of the present invention, R$^1$ is selected from:
aryl, aryl-C$_{1-4}$alkyl, heteroaryl, heteroaryl-C$_{1-4}$alkyl; wherein each alkyl is optionally substituted with one to three substituents independently selected from R$^a$, and each aryl and heteroaryl is optionally substituted with one to three substituents independently selected from R$^b$.

In one class of this embodiment, R$^1$ is selected from:
phenyl, phenyl-C$_{1-4}$alkyl, pyridyl, and pyridyl-C$_{1-4}$alkyl; wherein each alkyl is optionally substituted with one or two R$^a$ substituents and each phenyl or pyridyl is independently with one to three R$^b$ substituents.

In a subclass of this class of the present invention, R$^1$ is selected from:
phenyl, phenyl-C$_{1-4}$alkyl, pyridyl, and pyridyl-C$_{1-4}$alkyl;

wherein each phenyl and pyridyl is optionally substituted with one or two substituents selected from halogen, methyl, trifluoromethyl, cyano and methoxy, and each pyridyl is optionally present as the N-oxide.

In yet another subclass of this class of the present invention, R$^1$ is selected from:
phenyl, phenyl-C$_{1-4}$alkyl, pyridyl, and pyridyl-C$_{1-4}$alkyl;

wherein each phenyl and pyridyl is optionally substituted with one or two substituents selected from halogen, cyano and methoxy, and each pyridyl is optionally present as the N-oxide.

In one particular subclass of compounds of the present invention, R$^1$ is selected from: phenyl, phenyl-C$_{1-4}$alkyl, pyridyl, and pyridyl-C$_{1-4}$alkyl;

wherein each phenyl is optionally substituted with one or two substituents selected from halogen, and methoxy, and each pyridyl is optionally present as the N-oxide.

In still another subclass, R$^1$ is phenyl, unsubstituted or substituted with a halogen or cyano substituent.

In another embodiment of the present invention, R$^2$ is selected from:
C$_{1-10}$alkyl, C$_{3-10}$cycloalkyl-C$_{1-4}$alkyl, cycloheteroalkyl, cycloheteroalkyl-C$_{1-4}$alkyl, aryl, aryl-C$_{1-4}$alkyl, heteroaryl, and heteroaryl-C$_{1-4}$alkyl; wherein each alkyl is optionally substituted with one to three substituents independently selected from R$^a$, and each cycloalkyl, cycloheteroalkyl, aryl and heteroaryl is optionally substituted with one to three substituents independently selected from R$^b$.

In one class of this embodiment of the present invention, R$^2$ is selected from:
C$_{1-6}$alkyl, aryl, aryl-C$_{1-4}$alkyl, heteroaryl, and heteroaryl-C$_{1-4}$alkyl; wherein each alkyl is optionally substituted with one R$^a$ substituent, and each aryl and heteroaryl is optionally substituted with one to three substituents independently selected from R$^b$.

In a subclass of this class of the present invention, aryl is phenyl and heteroaryl is pyridyl in R$^2$.

In another subclass of this class of the present invention, R$^2$ is selected from:
isopropyl, isobutyl, n-propyl, n-butyl, cyclopropylmethyl, cyclobutylmethyl, cyclopentylmethyl, cyclohexylmethyl, phenyl, benzyl, phenylethyl, 3-phenylpropyl, 2-phenylpropyl, and pyridylmethyl;

wherein each cycloalkyl, aryl and heteroaryl is optionally substituted with one or two R$^b$ substituents selected from halogen, trifluoromethyl, cyano, methoxycarbonyl, and methoxy.

In yet another subclass, $R^2$ is benzyl, unsubstituted or substituted with halogen, cyano, trifluoromethyl or methoxy. In still another subclass, $R^2$ is 4-chlorobenzyl.

In another embodiment of the present invention, $R^3$ is selected from:
hydrogen, and $C_{1-4}$alkyl; wherein alkyl is optionally substituted with one or two substituents selected from $R^a$.

In one class of this embodiment of the present invention, $R^3$ is selected from: hydrogen, methyl, ethyl, and isopropyl.

In one subclass of this class of the present invention, $R^3$ is selected from hydrogen, methyl and ethyl.

In another subclass of this class of the present invention, $R^3$ is methyl.

In another embodiment of the present invention, $R^4$ is selected from:
hydrogen, and $C_{1-4}$alkyl; wherein alkyl is optionally substituted with one or two substituents selected from $R^a$.

In one class of this embodiment of the present invention, $R^4$ is selected from:
hydrogen, and methyl.

In one subclass of this class, $R^4$ is hydrogen.

In another embodiment of the present invention, $R^5$ is selected from:
$C_{1-10}$alkyl, $C_{2-10}$alkenyl, $C_{3-10}$cycloalkyl-$C_{1-10}$alkyl, cycloheteroalkyl-$C_{1-10}$alkyl, aryl-$C_{1-10}$alkyl, diaryl-$C_{1-10}$alkyl, aryl-$C_{2-10}$alkenyl, heteroaryl-$C_{1-10}$alkyl, —$OR^d$, $S(O)_m R^d$, and —$NR^cR^d$; wherein each alkyl or alkenyl is optionally substituted with one or two substituents independently selected from $R^a$, and each cycloalkyl, cycloheteroalkyl, aryl and heteroaryl is each optionally substituted with on to three substituents independently selected from $R^b$, provided that $R^5$ is not —CH═CH—COOH.

In one class of this embodiment of the present invention, $R^5$ is selected from:
$C_{1-8}$alkyl, $C_{2-8}$alkenyl, cycloheteroalkyl-$C_{1-8}$alkyl, aryl-$C_{1-8}$alkyl, diaryl-$C_{1-8}$alkyl, aryl-$C_{2-8}$alkenyl, heteroaryl-$C_{1-8}$alkyl, —$OR^d$, and —$NR^cR^d$, wherein each alkyl or alkenyl is optionally substituted with one or two substituents independently selected from $R^a$, and each cycloalkyl, cycloheteroalkyl, aryl and heteroaryl is each optionally substituted with on to three substituents independently selected from $R^b$, provided that $R^5$ is not —CH═CH—COOH.

In one subclass of this embodiment of the present invention, $R^5$ is selected from:
$C_{1-8}$alkyl, $C_{2-8}$alkenyl, cycloheteroalkyl-$C_{1-8}$alkyl, aryl-$C_{1-8}$alkyl, diaryl-$C_{1-4}$alkyl, aryl-$C_{2-8}$alkenyl, heteroaryl-$C_{1-8}$alkyl, —$OR^d$, and —$NR^cR^d$; wherein: each alkyl or alkenyl is optionally substituted with one or two substituents independently selected from $R^a$, and each cycloalkyl, cycloheteroalkyl, aryl and heteroaryl is each optionally substituted with one to three substituents independently selected from $R^b$ and wherein aryl is selected from phenyl and naphthyl; and heteroaryl is selected from pyridyl, pyrimidinyl, pyridazinyl, pyrazolyl, triazolyl, benzothiazolyl, benzoxazolinyl, isoxazolyl, indolyl and thiazolyl.

In a subclass of this class of the present invention, $R^5$ is selected from:
isopropyl, isobutyl, t-butyl, 1-ethyl-butyl, pentyl, benzyl, α-hydroxy-benzyl, α-amino-benzyl, α-dimethylamino-benzyl, α-methoxy-benzyl, α-hydroxy-diphenyl-methyl, 3-(aminosulfonyl)-propyl, 5-(t-butyloxycarbonylamino)-pentyl, anilino, anilino-methyl, t-butoxy, phenoxy, benzyloxy, 1-naphthyl-methyl, phenyl-ethyl, 3-phenyl-propyl, 3,3-diphenyl-propyl, 2-phenyl-ethylene, 1-phenyl-propyl, methoxymethyl, 3-benzoyl-propyl, 7-benzoyl-heptyl, 2-t-butoxy-ethyl, phenoxy-methyl, 1-(phenoxy)-ethyl, 2-(phenoxy)-isopropyl, 2-(pyridyloxy)-isopropyl, 2-(pyrimidinyloxy)-isopropyl, 2-(pyridazinyloxy)-isopropyl, cyclopropyl-methyl, cyclopentyl-methyl, 2-(cyclohexyloxy)-isopropyl, (1-indanone)-3-methyl, (2-thiazolyl)-S-methyl, (2-benzothiazolyl)-S-methyl, (2-benzoxazolyl)-S-methyl, benztriazolyl-methyl, 2-(benzothiazolyl)-ethyl, isoxazolyl-methyl, thiazolyl-methyl, triazolyl-methyl, 2-(triazolyl)-ethyl, pyrazolyl-methyl, 2-(pyrazolyl)-ethyl, and (3-(1-oxo-isoindolyl))-methyl;

wherein each alkyl is optionally substituted with one or two substituents independently selected from $R^a$, and each cycloalkyl, cycloheteroalkyl, aryl and heteroaryl is each optionally substituted with on to three substituents independently selected from $R^b$.

In yet another subclass of this class of the invention, $R^5$ is selected from:
$C_{1-8}$alkyl substituted with —$OR^d$ or $NR^cR^d$; $C_{2-8}$ alkenyl substituted with $OR^d$ or $NR^cR^d$; and phenyl-$C_{1-8}$ alkyl wherein phenyl is substituted with one to three $R^b$ substitutents.

In yet another subclass, $R^5$ is selected from:

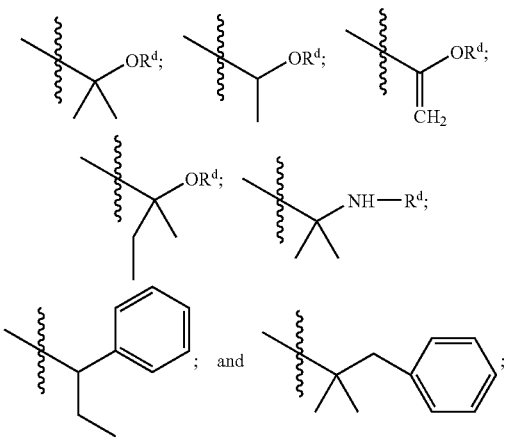

wherein the phenyl group may be substituted with one to three $R^b$ substituents.

In one subclass of the present invention, $R^5$ is

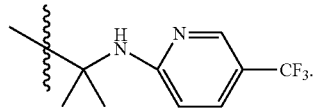

In another embodiment of the present invention, $R^6$ is selected from: methyl, hydroxyl, halogen, —CN, and —$NH_2$; wherein methyl is optionally substituted with one to three $R^a$ substituents In one class of this embodiment, $R^6$ is selected from: methyl, hydroxyl, halogen, and —CN.

In one embodiment of the present invention, each $R^a$ is independently selected from: —$OR^d$, —$NHS(O)_m R^d$, halogen, —$S(O)_m R^d$, —$S(O)_m NHR^d$, —$NR^cR^d$, —$C(O)R^d$, —$CO_2R^d$, —CN, —$C(O)NHR^d$, —$NHC(O)R^d$, —NHC(O) $OR^d$, —$NHC(O)NHR^d$, —$CF_3$, —$OCF_3$, and cycloheteroalkyl.

In one class of this embodiment of the present invention, each $R^a$ is independently selected from:
—$OR^d$, —$NHS(O)_2R^d$, halogen, —$SR^d$, —$SO_2R^d$, —$S(O)_2NH_2$, —$NHR^d$, —$N(CH_2CH_3)R^d$, —$C(O)R^d$, —$CO_2H$, —CN, —$C(O)NHR^d$, —$NHC(O)R^d$, —$NHC(O)OR^d$, —$NHC(O)NHR^d$, —$CF_3$, —$OCF_3$, and cycloheteroalkyl.

In one subclass of this class, each $R^a$ is independently selected from:
—$OR^d$, halogen, —CN, —$CF_3$, and —$OCF_3$.

In one embodiment of the present invention, each $R^b$ is independently selected from: —$OR^d$, —$NHS(O)_mR^d$, halogen, —$S(O)_mR^d$, —$S(O)_mNHR^d$, —$NHR^d$, —$C(O)R^d$, —$CO_2R^d$, —CN, —$C(O)NR^cR^d$, —$NHC(O)R^d$, —$NHC(O)OR^d$, —$NHC(O)NR^cR^d$, —$CF_3$, —$OCF_3$, cycloheteroalkyl, $C_{1-10}$alkyl, oxo, aryl, aryl$C_{1-4}$alkyl, heteroaryl, and heteroaryl$C_{1-4}$alkyl.

In one class of this embodiment of the present invention, each $R^b$ is independently selected from:
—$OR^d$, halogen, —CN, —$CF_3$, —$OCF_3$, —$S(O)_2R^d$, cycloheteroalkyl, $C_{1-4}$alkyl, oxo, phenyl, benzyl, and heteroaryl.

In one subclass of this class, each $R^b$ is independently selected from: methoxy, halogen, —CN, —$CF_3$, —$OCF_3$, —$S(O)_2R^d$, $C_{1-4}$alkyl, and oxo.

In another subclass of this class, each $R^b$ is independently selected from: halogen, —CN, —$CF_3$, —$OCF_3$, and methyl.

In still another subclass, each $R^b$ is independently selected from halogen and cyano.

In one embodiment of the present invention, each $R^c$ is independently selected from: hydrogen, and $C_{1-4}$alkyl; and each $R^d$ is independently selected from: hydrogen, $C_{1-4}$alkyl, $C_{2-6}$ alkenyl, cycloalkyl, cycloalkyl-$C_{1-4}$alkyl, cycloheteroalkyl, cycloheteroalkyl-$C_{1-4}$ alkyl, phenyl, heteroaryl, phenyl-$C_{1-4}$alkyl, and heteroaryl-$C_{1-4}$alkyl; or $R^c$ and $R^d$ together with the atom(s) to which they are attached form a heterocyclic ring of 4 to 7 members containing 0-2 additional heteroatoms independently selected from oxygen, sulfur and N—$R^g$, each $R^c$ and $R^d$ may be unsubstituted or substituted with one to three substituents selected from $R^h$.

In one class of this embodiment of the present invention, each $R^c$ is independently selected from:
hydrogen, and $C_{1-4}$alkyl; and
each $R^d$ is independently selected from: hydrogen, $C_{1-5}$alkyl, —$CH_2CH=CH_2$, cyclohexyl, cyclopentyl, cyclopropyl, cyclobutylmethyl, cyclopentylmethyl, cyclohexylmethyl, pyrrolidinyl, phenyl, thiazolyl, pyridyl, pyridazinyl, pyrimidinyl, benzothiazolyl, benzoxazolyl, triazolyl, benzyl, and pyridyl-methyl-, or $R^c$ and $R^d$ together with the atom(s) to which they are attached form a piperidinyl ring,
each $R^c$ and $R^d$ may be unsubstituted or substituted with one to three substituents selected from $R^h$.

In one subclass, $R^c$ is selected from hydrogen and methyl.

In another subclass, $R^d$ is selected from phenyl and heteroaryl, unsubstituted or substituted with one to three $R^h$ substituents.

In yet another subclass, $R^d$ is selected from phenyl, pyridinyl, pyrimidinyl and pyridazinyl, unsubstituted or substituted with one to three $R^h$ substituents.

In still another subclass, $R^d$ is selected from: phenyl, 3-cyanophenyl, 4-cyanophenyl, 2-fluorophenyl, 3-fluorophenyl, 3,4-difluorophenyl, 3,5-difluorophenyl, 3,4,5-trifluorophenyl, 3-chlorophenyl, 4-chlorophenyl, 3,4-dichlorophenyl, 3,5-dichlorophenyl, 3-chloro-4-fluorophenyl, 3-fluoro-4-chlorophenyl, 3-fluoro-5-chlorophenyl, 4-trifluoromethylphenyl, 3-trifluoromethylphenyl, 2-methoxyphenyl, 2-pyridyl, 3-pyridyl, 4-pyridyl, 5-trifluoromethyl-2-pyridyl, 4-trifluoromethyl-2-pyridyl, 6-chloro-2-pyridyl, 5-chloro-2-pyridyl, 4,6-dimethyl-2-pyridyl, 6-methyl-2-pyridyl, 5-methylsulfonyl-2-pyridyl, 2-pyrimidinyl, 5-chloro-2-pyrimidinyl, 4-trifluoromethyl-2-pyrimidinyl, 4-pyrimidinyl, 6-trifluoromethyl-4-pyrimidinyl, and 3-pyridazinyl.

In one embodiment of the present invention, each $R^g$ is independently selected from: $C_{1-4}$alkyl, and —$C(O)C_{1-4}$alkyl.

In one class of this embodiment, each $R^g$ is methyl or methylcarbonyl.

In one subclass of this class, each $R^g$ is methyl.

In one embodiment of the present invention, each $R^h$ is independently selected from: halogen, $C_{1-4}$alkyl, —O—$C_{1-4}$alkyl, —S—$(O)_mC_{1-4}$alkyl, —CN, —$CF_3$, and —$OCF_3$.

In one class of this embodiment, each $R^h$ is independently selected from: halogen, methyl, methoxy, methylthio, methylsulfonyl, —CN, —$CF_3$, and —$OCF_3$.

In one subclass, each Rh is independently selected from: halogen, methyl, methoxy, methylsulfonyl, —CN, —$CF_3$, and —$OCF_3$.

In one embodiment of the present invention, m is selected from zero and two.

In a class of this embodiment, m is two.

Particular novel compounds which may be employed in the methods, uses and compositions of the present invention, include: N-{[3-(4-chlorophenyl)-2-(3-bromophenyl)-1,2-dimethyl]propyl}-2-(5-trifluoromethyl-2-pyridyloxy)-2-methylpropanamide, N-{[3-(4-chlorophenyl)-2-cyano-2-phenyl-1-methyl]propyl}-2-(5-trifluoromethyl-2-pyridyloxy)-2-methylpropanamide, N-{[3-(4-chlorophenyl)-2-(3-bromophenyl)-2-hydroxy]propyl}-2-(5-trifluoromethyl-2-pyridyloxy)-2-methylpropanamide, N-{[3-(4-chlorophenyl-2-(3-bromophenyl)-2-fluoro-1(S)-methyl]propyl}-2-(5-trifluoromethyl-2-pyridyloxy)-2-methylpropanamide, N-{[3-(4-chlorophenyl)-2-(3-cyanophenyl)-2-fluoro-1(S)-methyl]propyl}-2-(5-trifluoromethyl-2-pyridyloxy)-2-methylpropanamide, N-{[3-(4-chlorophenyl)-2-(3-cyanophenyl)-1,2-dimethyl]propyl}-2-(5-trifluoromethyl-2-pyridyloxy)-2-methylpropanamide, N-{[3-(4-chlorophenyl)-2-(3-bromophenyl)-2-hydroxy-1(S)-methyl]propyl}-2-(5-trifluoromethyl-2-pyridyloxy)-2-methylpropanamide, N-{[3-(4-chlorophenyl)-2-(3-bromophenyl)-2-hydroxy-1(R)-methyl]propyl}-2-(5-trifluoromethyl-2-pyridyloxy)-2-methylpropanamide, 1-{[3-(4-chlorophenyl)-2-(3-cyanophenyl)-2-fluoro-1(S)-methyl]propyl}-3-[2-(phenyl)ethyl)urea, 1-{[3-(4-chlorophenyl)-2-(3-cyanophenyl)-2-hydroxy-1(S)-methyl]propyl}-3-[2-(4-chlorophenyl)ethyl)urea, 1-{[3-(4-chlorophenyl)-2-(3-cyanophenyl)-2-hydroxy-1(S)-methyl]propyl}-3-methyl-3-[2-(phenyl)ethyl)urea, 1-{[3-(4-cholorphenyl)-2-(3-cyanophenyl)-2-hydroxy-1(S)-methyl]propyl}-3-[1-(4-chlorophenyl)ethyl)urea, N-{[3-(4-chlorophenyl)-2-(3-cyanophenyl)-2-hydroxy-1(S)-methyl]propyl}-2-phenylbutanamide, N-{[3-(4-chlorophenyl)-2-(3-cyanophenyl)-2-fluoro-1(S)-methyl]propyl}-1-ethyl-cyclobutanecarboxamide, N-{[3-(4-chlorophenyl)-2-(3-cyanophenyl)-2-hydroxy-1(S)-methyl]propyl}-1-phenyl-cyclobutanecarboxamide, N-{[3-(4-chlorophenyl)-2-(3-cyanophenyl)-2-hydroxy-1(S)-methyl]propyl}-2-phenyl-butanamide, and pharmaceutically acceptable salts thereof.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic or bridged saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic cycloheteroalkyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, imidazothiazolyl, and the like. The heteroaryl ring may be substituted on one or more carbon or nitrogen atoms "Cycloheteroalky" means mono- or bicyclic or bridged saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "cycloheteroalkyl" include pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl,5,6-dihydroimidazo[2,1-b]thiazolyl, tetrahydrohydroquinolinyl, morpholinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). The term also includes bridged rings such as 5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, and azabicyclo[2.2.1]heptanyl. The cycloheteroalkyl ring may be substituted on the ring carbons and/or the ring nitrogens.

"Halogen" includes fluorine, chlorine, bromine and iodine.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

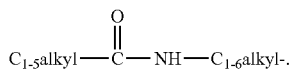

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are modulators of the CB1 receptor. In particular, the compounds of structural formula I are antagonists or inverse agonists of the CB1 receptor.

An "agonist" is a compound (hormone, neurotransmitter or synthetic compound) which binds to a receptor, inducing a conformational change in the receptor which, in turn, produces a response such as contraction, relaxation, secretion, change in enzyme activity, etc. similar to that elicited by the physiologically relevant agonist ligand(s) for that receptor. An "antagonist" is a compound which attenuates the effect of an agonist. An "inverse agonist" is a compound which acts on a receptor but produces the opposite effect produced by the agonist of the particular receptor.

Compounds of this invention are modulators of the CB1 receptor and as such are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of obesity or eating disorders associated with excessive food intake and complications associated therewith. The compounds are also useful for the treatment of constipation and chronic intestinal pseudo-obstruction. The compounds are also useful for the treatment of cirrhosis of the liver. The compounds are also useful for the treatment of asthma.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The utilities of the present compounds in these diseases or disorders may be demonstrated in animal disease models that have been reported in the literature. The following are examples of such animal disease models: a) suppression of food intake and resultant weight loss in rats (Life Sciences 1998, 63, 113-117); b) reduction of sweet food intake in marmosets (Behavioural Pharm. 1998, 9, 179-181); c) reduction of sucrose and ethanol intake in mice (Psychopharm. 1997, 132, 104-106); d) increased motor activity and place conditioning in rats (Psychopharm. 1998, 135, 324-332; Psychopharmacol 2000, 151: 25-30); e) spontaneous locomotor activity in mice (J. Pharm. Exp. Ther. 1996, 277, 586-594); f) reduction in opiate self-administration in mice (Sci. 1999, 283, 401-404); g) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the gunea-pig." Eur. J. Pharmacol., 282, 243 (1995)); h) mediation of the vasodilated state in advanced liver cirrhosis induced by carbon tetrachloride (Nature Medicine, 2001, 7 (7), 827-832); i) amitriptyline-induced constipation in cynomolgus monkeys is beneficial for the evaluation of laxatives (Biol. Pharm. Bulletin (Japan), 2000, 23(5), 657-9); j) neuropathology of paediatric chronic intestinal pseudo-obstruction and animal models related to the neuropathology of paediatric chronic intestinal pseudo-obstruction (Journal of Pathology (England), 2001, 194 (3), 277-88).

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for preventive use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 1000 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 750 or 1000 milligrams of the active ingredient for the symptomatic adjustment of the dosage to the patient to be treated.

For the treatment of diseases of the eye, ophthalmic preparations for ocular administration comprising 0.001-1% by weight solutions or suspensions of the compounds of Formula I in an acceptable ophthalmic formulation may be used.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. In particular, the term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those well known to those of ordinary skill in that art. To be administered in the form of a transdermal delivery system, the dosage administration will, of course, be continuous rather than intermittent throughout the dosage regimen.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from 0.01 to 1,000 mg, particularly 0.01, 0.05, 0.1, 0.5, 1, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated, and each cachet or capsule contains from about 0.01 to 1,000 mg, particularly 0.01, 0.05, 0.1, 0.5, 1.0, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Capsule | mg/capsule |
|---|---|
| Compound of Formula I | 25 |
| Lactose Powder | 573.5 |
| Magnesium Stearate | 1.5 |
| | 600 |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: antipsychotic agents, cognition enhancing agents, anti-migraine agents, anti-asthmatic agents, antiinflammatory agents, axiolytics, anti-Parkinson's agents, anti-epileptics, anorectic agents, and serotonin reuptake inhibitors, which may be administered separately or in the same pharmaceutical compositions.

The present invention also provides a method for the treatment or prevention of a CB1 receptor modulator mediated disease, which method comprises administration to a patient in need of such treatment or at risk of developing a CB1 receptor modulator mediated disease of an amount of a CB1 receptor modulator and an amount of one or more active ingredients, such that together they give effective relief.

In a further aspect of the present invention, there is provided a pharmaceutical composition comprising a CB1 receptor modulator and one or more active ingredients, together with at least one pharmaceutically acceptable carrier or excipient.

Thus, according to a further aspect of the present invention there is provided the use of a CB1 receptor modulator and one or more active ingredients for the manufacture of a medicament for the treatment or prevention of a CB1 receptor modulator mediated disease. In a further or alternative aspect of the present invention, there is therefore provided a product comprising a CB1 receptor modulator and one or more active ingredients as a combined preparation for simultaneous, separate or sequential use in the treatment or prevention of CB1 receptor modulator mediated disease. Such a combined preparation may be, for example, in the form of a twin pack.

It will be appreciated that for the treatment or prevention of eating disorders, including obesity, bulimia nervosa and compulsive eating disorders, a compound of the present invention may be used in conjunction with other anorectic agents.

The present invention also provides a method for the treatment or prevention of eating disorders, which method comprises administration to a patient in need of such treatment an amount of a compound of the present invention and an amount of an anoretic agent, such that together they give effective relief.

Suitable anoretic agents for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention also provides a method for the treatment or prevention of obesity, which method comprises administration to a patient in need of such treatment an amount of a compound of the present invention and an amount of an SSRI, such that together they give effective relief.

Suitable selective serotonin reuptake inhibitors of use in combination with a compound of the present invention include: fluoxetine, fluvoxamine, paroxetine and sertraline, and pharmaceutically acceptable salts thereof.

The present invention also provides a method for the treatment or prevention of obesity, which method comprises administration to a patient in need of such treatment or prevention, an amount of a compound of the present invention and an amount of growth hormone secretagogues such as those disclosed and specifically described in U.S. Pat. No. 5,536,716; melanocortin agonists such as Melanotan II or those described in WO 99/64002, WO 00/74679, WO 01/70708, WO 01/70337, WO 01/91752 and WO 02/15909; β-3 agonists such as those disclosed and specifically described in patent publications WO94/18161, WO95/29159, WO97/46556, WO98/04526 and WO98/32753; 5HT-2 agonists; orexin antagonists; melanin concentrating hormone antagonists; galanin antagonists; CCK agonists; GLP-1 agonists; corticotropin-releasing hormone agonists; NPY-5 antagonists; Y1 antagonists, histamine receptor-3 (H3) modulators, melanin concentrating hormone-I receptor (MCH1R) antagonists, melanin concentrating hormone-2 receptor (MCH2R) agonists and antagonists and/or phosphodiesterase-3B (PDE3B) inhibitors, such that together they give effective relief.

It will be appreciated that for the treatment or prevention of obesity, the compounds of the present invention may also be used in combination with an opioid antagonist.

The present invention also provides a method for the treatment or prevention of obesity, which method comprises administration to a patient in need of such treatment an amount of a compound of the present invention and an amount of an opioid antagonist, such that together they give effective relief.

Suitable opioid antagonists of use in combination with a compound of the present invention include: naloxone, naltrexone, and nalmefene, and pharmaceutically acceptable salts thereof.

It will be appreciated that for the treatment or prevention of obesity, the compounds of the present invention may also be used in combination with inhibitors of the enzyme 11β-HSD1. Generally, glucocorticoid concentrations are modulated by tissue-specific 11β-hydroxysteroid dehydrogenase enzymes. The 11β-hydroxysteroid dehydrogenase type 1 enzyme (11β-HSD1) is a low affinity enzyme that generally uses NADP+ as a cofactor rather than NAD+ (Agarwal et al., 1989). In vitro studies have shown that 11β-HSD1 is capable of acting as both a reductase and a dehydrogenase. However, 11β-HSD1 in vivo generally acts as a reductase, converting 11-ketoglucocorticoids, such as cortisone, to 11β-hydroxyglucocorticoids such as cortisol.

Excessive levels of cortisol have been associated with obesity, perhaps due to increased hepatic gluconeogenesis. Thus, the administration of an effective amount of an 11β-HSD1 inhibitor in combination with a CB1 antagonist of the present invention may be useful in the treatment or control of obesity. Particular inhibitors of 11β-HSD1 useful in combination with the compounds of the present invention include: 3-(1-adamantyl)-4-ethyl-5-(ethylthio)-4H-1,2,4-triazole, 3-(1-adamantyyl)-5-(3,4,5-trimethoxyphenyl)-4-methyl-4H-1,2,4-triazole, and 3-adamantanyl-4,5,6,7,8,9,10,11,12,3a-decahydro-1,2,4-triazolo[4,3-a][11]annulene.

"Obesity" is a condition in which there is an excess of body fat. The operational definition of obesity is based on the Body Mass Index (BMI), which is calculated as body weight per height in meters squared (kg/m$^2$). "Obesity" refers to a condition whereby an otherwise healthy subject has a Body Mass Index (BMI) greater than or equal to 30 kg/m$^2$, or a condition whereby a subject with at least one co-morbidity has a BMI greater than or equal to 27 kg/m$^2$. An "obese subject" is an otherwise healthy subject with a Body Mass Index (BMI) greater than or equal to 30 kg/m$^2$ or a subject with at least one co-morbidity with a BMI greater than or equal to 27 kg/m$^2$. A "subject at risk for obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asian countries, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes. Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable neurokinin-1 receptor antagonists may be peptidal or non-peptidal in nature, however, the use of a non-peptidal neurokinin-1 receptor antagonist is preferred. In a preferred embodiment, the neurokinin-1 receptor antagonist is a CNS-penetrant neurokinin-1 receptor antagonist. In addition, for convenience the use of an orally active neurokinin-1 receptor antagonist is preferred. To facilitate dosing, it is also preferred that the neurokinin-1 receptor antagonist is a long acting neurokinin-1 receptor antagonist. An especially preferred class of neurokinin-1 receptor antagonists of use in the present invention are those compounds which are orally active and long acting.

Neurokinin-1 receptor antagonists of use in the present invention are fully described, for example, in U.S. Pat. Nos. 5,162,339, 5,232,929, 5,242,930, 5,373,003, 5,387,595, 5,459,270, 5,494,926, 5,496,833, 5,637,699; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, 97/49710, 98/24438-98/24441, 98/24442-98/24445, 02/16343, and 02/16344; and in British Patent Publication Nos. 2 266 529, 2 268 931, 2 269 170, 2 269 590, 2 271 774, 2 292 144, 2 293 168, 2 293 169, and 2 302 689.

Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperdin-3-amine; 2-(S)-(3,5-bis(trifluoromethyl)benzyloxy)-3(S)-(4-fluorophenyl)-4-(3-(5-oxo-1H,4H-1,2,4-triazolo)methyl)morpholine; 2-(R)-(1-(R)-(3,5-bis (trifluoromethyl)phenyl)ethoxy)-4-(3-(5-oxo-1H,4H-1,2,4-triazolo)methyl)-3-(S)-phenyl-morpholine; 2-(S)-(3,5-bis (trifluoromethyl)benzyloxy)-4-(3-(5-oxo-1H,4H-1,2,4-triazolo)methyl)-3-(S)-phenyl-morpholine; 2-(R)-(1-(R)-(3, 5-bis(trifluoromethyl)phenyl)ethoxy)-3-(S)-(4-fluorophenyl)-4-(3-(5-oxo-1H,4H-1,2,4-triazolo)methyl) morpholine; 2-(R)-(1-(R)-(3,5-bis(trifluoromethyl)phenyl) ethoxy)-4-(5-(N,N-dimethylamino)methyl-1,2,3-triazol-4-yl)methyl-3-(S)-phenylmorpholine; 2-(R)-(1-(R)-(3,5-bis (trifluoromethyl)phenyl)ethoxy)-4-(5-(N,N-dimethylamino) methyl-1,2,3-triazol-4-yl)methyl-3-(S)-(4-fluorophenyl) morpholine; (3S,5R,6S)-3-[2-cyclopropoxy-5-(trifluoromethoxy)phenyl]-6-phenyl-1-oxa-7-aza-spiro[4.5] decane; (3R,5R,6S)-3-[2-cyclopropoxy-5-(trifluoromethoxy)phenyl]-6-phenyl-1-oxa-7-aza-spiro[4.5] decane; 2-(R)-(1-(S)-(3,5-bis(trifluoromethyl)phenyl)-2-hydroxyethoxy)-3-(S)-(4-fluorophenyl)-4-(1,2,4-triazol-3-yl)methylmorpholine; 2-(R)-(1-(R)-(3,5-bis (trifluoromethyl)phenyl) ethoxy)-3-(S)-(4-fluorophenyl)-4-(3-(4-monophosphoryl-5-oxo-1H-1,2,4-triazolo)methyl) morpholine; 2-(R)-(1-(R)-(3,5-bis(trifluoromethyl)phenyl) ethoxy)-3-(S)-(4-fluorophenyl)-4-(3-(1-monophosphoryl-5-oxo-1H-1,2,4-triazolo)methyl)morpholine; 2-(R)-(1-(R)-(3, 5-bis(trifluoromethyl)phenyl)ethoxy)-3-(S)-(4-fluorophenyl)-4-(3-(2-monophosphoryl-5-oxo-1H-1,2,4-triazolo)methyl)morpholine; 2-(R)-(1-(R)-(3,5-bis (trifluoromethyl)phenyl)ethoxy)-3-(S)-(4-fluorophenyl)-4-(3-(5-oxyphosphoryl-1H-1,2,4-triazolo)methyl)morpholine; 2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine; 2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine; or a pharmaceutically acceptable salt thereof.

Suitable atypical anti-depressants include: bupropion, lithium, nefazodone, trazodone and viloxazine, and pharmaceutically acceptable salts thereof.

Suitable classes of anti-anxiety agents include benzodiazepines and $5\text{-HT}_{1A}$ agonists or antagonists, especially $5\text{-HT}_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable $5\text{-HT}_{1A}$ receptor agonists or antagonists include, in particular, the $5\text{-HT}_{1A}$ receptor partial agonists buspirone, flesinoxan, gepirone and ipsapirone, and pharmaceutically acceptable salts thereof.

Suitable corticotropin releasing factor (CRF) antagonists include those previously discussed herein.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance abuse disorders" include substance-induced anxiety disorder with onset during withdrawal; substance-induced mood disorder with onset during withdrawal; and substance-induced sleep disorder with onset during withdrawal.

It will be appreciated that a combination of a conventional antipsychotic drug with a CB1 receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antipychotic agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

Thus, according to a further aspect of the present invention there is provided the use of a CB1 receptor modulator and an antipsychotic agent for the manufacture of a medicament for the treatment or prevention of mania.

The present invention also provides a method for the treatment or prevention of mania, which method comprises administration to a patient in need of such treatment or at risk of developing mania of an amount of a CB1 receptor modulator and an amount of an antipsychotic agent, such that together they give effective relief.

In a further aspect of the present invention, there is provided a pharmaceutical composition comprising a CB1 receptor modulator and an antipsychotic agent, together with at least one pharmaceutically acceptable carrier or excipient.

It will be appreciated that the CB1 receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a CB1 receptor modulator and an antipsychotic agent as a combined preparation for simultaneous, separate or sequential use in the treatment or prevention of mania.

It will be appreciated that when using a combination of the present invention, the CB1 receptor modulator and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the CB1 receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of CB1 receptor modulators in combination with an antipsychotic agent in the treatment or prevention of hypomania.

It will be appreciated that a combination of a conventional antipsychotic drug with a CB1 receptor modulator may provide an enhanced effect in the treatment of schizophrenic disorders. Such a combination would be expected to provide for a rapid onset of action to treat schizophrenic symptoms thereby enabling prescription on an "as needed basis". Furthermore, such a combination may enable a lower dose of the CNS agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a CB1 receptor modulator include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with a CB1 receptor modulator is the 5-$HT_{2A}$ receptor antagonists, examples of which include MDL100907 and fananserin. Also of use in combination with a CB1 receptor modulator are the serotonin dopamine antagonists (SDAs) which are believed to combine 5-$HT_{2A}$ and dopamine receptor antagonist activity, examples of which include olanzapine and ziperasidone.

It will be appreciated that a combination of a conventional anti-asthmatic drug with a CB1 receptor modulator may provide an enhanced effect in the treatment of asthma.

Thus, according to a further aspect of the present invention there is provided the use of a CB1 receptor modulator and an anti-asthmatic agent for the manufacture of a medicament for the treatment or prevention of asthma.

The present invention also provides a method for the treatment or prevention of asthma, which method comprises administration to a patient in need of such treatment an amount of a compound of the present invention and an amount of an anti-asthmatic agent, such that together they give effective relief.

Suitable anti-asthmatic agents of use in combination with a compound of the present invention include, but are not limited to: (a) VLA-4 antagonists such as natalizumab and the compounds described in U.S. Pat. No. 5,510,332, WO97/03094, WO97/02289, WO96/40781, WO96/22966, WO96/20216, WO96/01644, WO96/06108, WO95/15973 and WO96/31206; (b) steroids and corticosteroids such as beclomethasone, methylprednisolone, betamethasone, prednisone, dexamethasone, and hydrocortisone; (c) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (d) non-steroidal anti-asthmatics including β2-agonists (such as terbutaline, metaproterenol, fenoterol, isoetharine, albuterol, bitolterol, salmeterol, epinephrine, and pirbuterol), theophylline, cromolyn sodium, atropine, ipratropium bromide, leukotriene antagonists (such as zafirlukast, montelukast, pranlukast, iralukast, pobilukast, and SKB-106,203), and leukotriene biosynthesis inhibitors (such as zileuton and BAY-1005); (e) anti-cholinergic agents including muscarinic antagonists (such as ipratropium bromide and atropine); (f antagonists of the chemokine receptors, especially CCR-1, CCR-2, and CCR-3; (g) immunosuppressants such as cyclosporin, tacrolimus, rapamycin and other FK-506 type immunosuppressants; (h) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (i) cyclooxygenase-2 (COX-2) inhibitors such as celecoxib; (j) anti-diabetic agents such as insulin, sulfonylureas, biguanides (metformin), a-glucosidase inhibitors (acarbose) and glitazones (troglitazone, pioglitazone, englitazone, MCC-555, BRL49653 and the like); (k) preparations of interferon beta (interferon beta-1a, interferon beta-1b); (l) other compounds such as 5-aminosalicylic acid and prodrugs thereof, and pharmaceutically acceptable salts thereof.

It will be appreciated that a combination of a conventional anti-constipation drug with a CB1 receptor modulator may provide an enhanced effect in the treatment of constipation.

Thus, according to a further aspect of the present invention there is provided the use of a CB1 receptor modulator and an anti-constipation agent for the manufacture of a medicament for the treatment or prevention of constipation.

The present invention also provides a method for the treatment or prevention of constipation, which method comprises administration to a patient in need of such treatment an amount of a compound of the present invention and an amount of an anti-constipation agent, such that together they give effective relief.

It will be appreciated that a combination of a conventional anti-constipation drug with a CB1 receptor modulator may provide an enhanced effect in the treatment of chronic intestinal pseudo-obstruction.

Thus, according to a further aspect of the present invention there is provided the use of a CB1 receptor modulator and an anti-constipation agent for the manufacture of a medicament for the treatment or prevention of chronic intestinal pseudo-obstruction.

The present invention also provides a method for the treatment or prevention of chronic intestinal pseudo-obstruction, which method comprises administration to a patient in need of such treatment an amount of a compound of the present invention and an amount of an anti-constipation agent, such that together they give effective relief.

Suitable anti-constipation agents of use in combination with a compound of the present invention include, but are not limited to, osmotic agents, laxatives and detergent laxatives (or wetting agents), bulking agents, and stimulants; and pharmaceutically acceptable salts thereof.

A particularly suitable class of osmotic agents include, but are not limited to sorbitol, lactulose, polyethylene glycol, magnesium, phosphate,and sulfate; and pharmaceutically acceptable salts thereof.

A particularly suitable class of laxatives and detergent laxatives, include, but are not limited to, magnesium, and docusate sodium; and pharmaceutically acceptable salts thereof.

A particularly suitable class of bulking agents include, but are not limited to, psyllium, methylcellulose, and calcium polycarbophil; and pharmaceutically acceptable salts thereof.

A particularly suitable class of stimulants include, but are not limited to, anthroquinones, and phenolphthalein; and pharmaceutically acceptable salts thereof.

It will be appreciated that a combination of a conventional anti-cirrhosis drug with a CB1 receptor modulator may provide an enhanced effect in the treatment of cirrhosis of the liver.

Thus, according to a further aspect of the present invention there is provided the use of a CB1 receptor modulator and an anti-cirrhosis agent for the manufacture of a medicament for the treatment or prevention of cirrhosis of the liver.

The present invention also provides a method for the treatment or prevention of cirrhosis of the liver, which method comprises administration to a patient in need of such treatment an amount of a compound of the present invention and an anti-cirrhosis agent, such that together they give effective relief.

Suitable anti-cirrhosis agents of use in combination with a compound of the present invention include, but are not limited to, corticosteroids, penicillamine, colchicine, interferon-γ, 2-oxoglutarate analogs, prostaglandin analogs, and other anti-inflammatory drugs and antimetabolites such as azathioprine, methotrexate, leflunamide, indomethacin, naproxen, and 6-mercaptopurine; and pharmaceutically acceptable salts thereof.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations used in the following Schemes and Examples: aq.: aqueous; API-ES: atmospheric pressure ionization-electrospray (mass spectrum term); DEAD: diethyl azodicarboxylate; DMAP: 4-dimethylaminopyridine; DMF: dimethylformamide; DMSO: dimethylsulfoxide; EDC: 1-ethyl-3-(3-dimethylaminopropyl)-carbodiimide hydrochloride; EPA: ethylene polyacrylamide (a plastic); EtOAc: ethyl acetate; g: gram; h: hours' HOBt: 1-hydroxybenzotriazole; HPLC: high pressure liquid chromatography; HPLC/MS: high pressure liquid chromatography/mass spectrum; in vacuo: rotoevaporation; LC: Liquid chromatography; LC/MS, LC-MS: liquid chromatography-mass spectrum; LDA: lithium diisopropyl amide; M: molar; Me: methyl; MeOH: methanol; MHz: megahertz; min: minute; mL: milliliter; mmol: millimole; MS or ms: mass spectrum; N: normal; NaHMDS: sodium hexamethyldisilazide; NMR: nuclear magnetic resonance; PyBOP: (benzotriazol-1-yloxy) tripyrrolidinophosphonium hexafluorophosphate; $R_t$: retention time; rt or RT: room temperature; TFA: trifluoroacetic acid; THF: tetrahydrofuran; TLC: thin layer chromatography.

Compounds of the present invention may be prepared by procedures illustrated in the accompanying scheme.

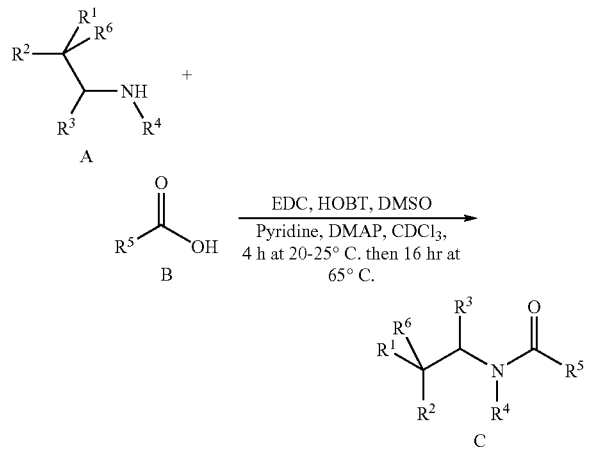

Scheme 1.

In Scheme 1, an appropriately substituted amine A is reacted with a carboxylic acid B under standard amide bond forming conditions to afford the arylamide C.

In order to illustrate the invention, the following examples are included. These examples do not limit the invention. They are only meant to suggest a method of reducing the invention to practice. Those skilled in the art may find other methods of practicing the invention which are readily apparent to them. However, those methods are also deemed to be within the scope of this invention.

General Procedures.

The LC/MS analyses were preformed using a MICROMASS ZMD mass spectrometer coupled to an AGILENT 1100 Series HPLC utilizing a YMC ODS-A 4.6×50 mm column eluting at 2.5 mL/min with a solvent gradient of 10 to 95% B over 4.5 min, followed by 0.5 min at 95% B: solvent A=0.06% TFA in water; solvent B=0.05% TFA in acetonitrile. $^1$H-NMR spectra were obtained on a 500 MHz VARIAN Spectrometer in CDCl$_3$ or CD$_3$OD as indicated and chemical shifts are reported as δ using the solvent peak as reference and coupling constants are reported in hertz (Hz).

REFERENCE EXAMPLE 1

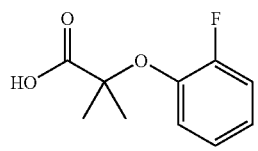

2-(2-Fluorophenyloxy)-2-methylpropionic Acid

To a solution of 2-fluorophenol (2.0 g, 18 mmol) and 1,1,1-trichloro-2-methyl-2-propanol (7.9 g, 45 mmol) in acetone (100 mL) was added sodium hydroxide (7.1 g, 0.18 mol), and an ice-water bath was periodically applied to maintain a gentle reflux. After the reflux subsided, the reaction was stirred for one additional hour. The volatile materials were removed on a rotary evaporator, and the residue partitioned between ether (100 mL), hexane (100 mL) and water (200 mL). The aqueous layer was separated and acidified with concentrated hydrochloric acid (pH=2), and extracted with ether (3×100 mL). The combined extracts were dried over anhydrous magnesium sulfate, filtered, and concentrated to dryness to give the title compound, which was used without further purification. $^1$H NMR (500 MHz, CD$_3$OD): δ 7.15-7.05 (m, 4H), 1.56 (s, 6H). LC-MS: m/e 199 (M+1)$^+$ (2.3 min).

The acids of Reference Examples 2-12 were prepared following the procedures described for Reference Example 1 substituting 2-fluorophenol with appropriately substituted phenols.

REFERENCE EXAMPLE 2

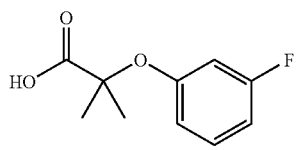

2-(3-Fluorophenyloxy)-2-methylpropionic Acid

¹H NMR (500 MHz, CD₃OD): δ 7.26 (ddd, 1H), 6.77-6.70 (m, 2H), 6.64 (dt, 1H), 1.59 (s, 6H). LC-MS: m/e 199 (M+1)⁺, (2.4 min).

REFERENCE EXAMPLE 3

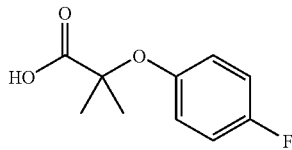

2-(4-Fluorophenyloxy)-2-methylpropionic Acid

¹H NMR (500 MHz, CD₃OD): δ 7.02-6.92 (m, 4H), 1.54 (s, 6H).

REFERENCE EXAMPLE 4

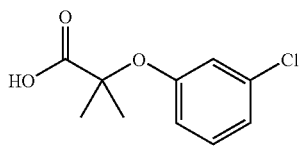

2-(3-Chlorophenyloxy)-2-methylpropionic Acid

¹H NMR (500 MHz, CD₃OD): δ 7.23 (t, 1H), 7.00 (dd, 1H), 6.93 (t, 1H), 6.84 (dd, 1H), 1.59 (s, 6H). LC-MS: m/e 215 (M+1)⁺, (2.7 min).

REFERENCE EXAMPLE 5

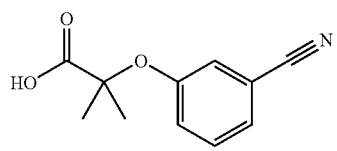

2-(3-Cyanophenyloxy)-2-methylpropionic Acid

¹H NMR (500 MHz, CD₃OD): δ 7.44 (dd, 1H), 7.36 (d, 1H), 7.22 (m, 2H), 1.62 (s, 6H).

REFERENCE EXAMPLE 6

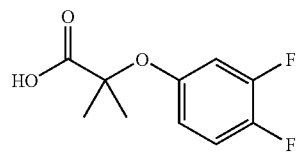

2-(3,4-Difluorophenyloxy)-2-methylpropionic Acid

¹H NMR (500 MHz, CD₃OD): δ 7.16 (q, 1H), 6.86 (dddd, 1H), 6.72 (m, 1H), 1.57 (s, 6H). LC-MS: m/e 217 (M+1)⁺, (2.5 min).

REFERENCE EXAMPLE 7

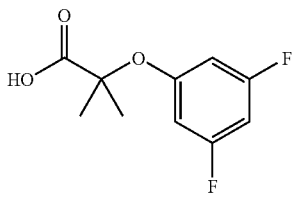

2-(3,5-Difluorophenyloxy)-2-methylpropionic Acid

¹H NMR (500 MHz, CD₃OD): δ 6.56 (m, 1H), 6.47 (m, 2H), 1.60 (s, 6H).

REFERENCE EXAMPLE 8

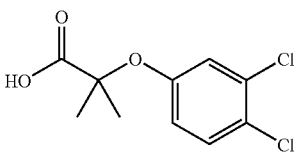

2-(3,4-Dichlorophenyloxy)-2-methylpropionic Acid

¹H NMR (500 MHz, CD₃OD): δ 7.40 (dd, 1H), 7.07 (d, 1H), 6.85 (dd, 1H), 1.60 (s, 6H).

REFERENCE EXAMPLE 9

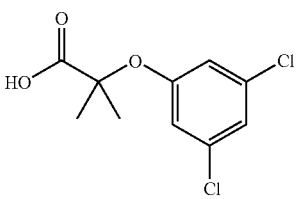

2-(3,5-Dichlorophenyloxy)-2-methylpropionic Acid $^{1}$H NMR (500 MHz, CD$_3$OD): δ 7.05 (t, 1H), 6.84 (d, 2H), 1.60 (s, 6H).

REFERENCE EXAMPLE 10

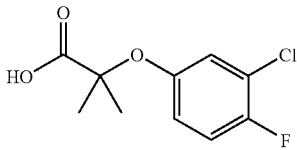

2-(3-Chloro-4-fluorophenyloxy)-2-methylpropionic Acid $^{1}$HNMR(500 MHz, CD$_3$OD): δ 7.16 (t, 1H), 7.05 (dd, 1H), 6.90 (td, 1H), 1.57 (s, 6H).

REFERENCE EXAMPLE 11

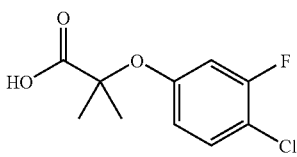

2-(4-Chloro-3-fluorophenyloxy)-2-methylpropionic Acid $^{1}$H NMR (500 MHz, CD$_3$OD): δ 7.36 (t, 1H), 6.80 (dd, 1H), 6.74 (dd, 1H), 1.60 (s, 6H).

REFERENCE EXAMPLE 12

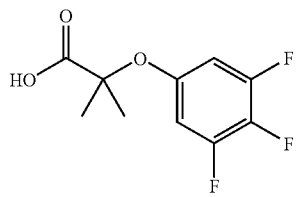

2-(3,4,5-Trifluorophenyloxy)-2-methylpropionic Acid $^{1}$H NMR (500 MHz, CD$_3$OD): δ 6.68 (dd, 2H), 1.60 (s, 6H).

REFERENCE EXAMPLE 13

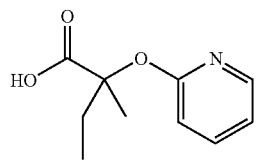

2-(2-Pyridyloxy)-2-methylbutanoic Acid

Step A: Benzyl 2-(2-Pyridyloxy)propionate

To a mixture of 2-hydroxypyridine (2.9 g, 30 mmol), benzyl lactate (5.0 g, 21 mmol) and triphenylphosphine (12 g, 47 mmol) in 100 mL of methylene chloride was added diethylazodicarboxylate (7.8 mL, 45 mmol) at 0° C. The reaction was allowed to warm to room temperature for 4 h. The resulting mixture was diluted with hexane (100 mL) and concentrated with 20 g of silica gel. The material was loaded onto a silica gel column, which was eluted with 10% ethyl acetate in hexane to give the title compound. $^{1}$H NMR (500 MHz, CD$_3$OD): δ 8.00 (dd, 1H), 7.68 (ddd, 1H), 7.36-7.28 (m, 5 H), 6.94 (dd, 1H), 6.84 (dd, 1H), 5.30 (q, 1H), 5.18 (s, 2H), 1.59 (d, 3H). LC-MS: m/e 258 (M+H)$^{+}$ (3.3 min).

Step B: Benzyl 2-(2-Pyridyloxy)-2-methylbutanoate.

To a solution of benzyl 2-(2-pyridyloxy)propionate (1.6 g, 6.2 mmol) and ethyl iodide (1.5 mL, 25 mmol) in 10 mL of anhydrous tetrahydrofuran at −78° C. was added sodium hexamethyldisilazide (1 M in tetrahydrofuran, 9.3 mL, 9.3 mmol) (potassium hexamethyldisilazide in toluene may be used with similar results). The reaction was allowed to warm to room temperature over 2 h and was partitioned between saturated ammonium chloride (100 mL) and ethyl acetate (100 mL). The organic layer was separated and the aqueous layer extracted with ethyl acetate (2×50 mL). The combined organic extracts were dried over anhydrous sodium sulfate, filtered, and concentrated to dryness, and the residue was purified by flash column chromatography on silica gel eluted with 10% ethyl acetate in hexane to give the title compound. $^{1}$H NMR (500 MHz, CD$_3$OD): δ 7.87 (dd, 1H), 7.63 (ddd, 1H), 7.27 (m, 3H), 7.18. (m, 2H), 6.85 (dd, 1H), 6.74 (dd, 1H), 5.08 (ABq, 2H), 2.13 (m, 1H), 1.94 (m, 1H), 1.65 (s, 3H), 0.95 (s, 3H), LC-MS: m/e 286 (M+H)$^{+}$ (3.8 min).

Step C: 2-(2-Pyridyloxy)-2-methylbutanoic Acid

A mixture of benzyl 2-(2-pyridyloxy)-2-methylbutanoate (1.6 g, 5.5 mmol) and 10% palladium on carbon (50 mg) in 50 mL of methanol was degassed and filled with hydrogen using a balloon. After stirring at room temperature overnight, the reaction mixture was filtered through CELITE diatomaceous earth and washed with methanol (20 mL), and the filtrate was concentrated to dryness to give the title compound. $^{1}$H NMR (500 MHz, CD$_3$OD): δ 8.03 (dd, 1H), 7.64 (ddd, 1H), 6.89

(dd, 1H), 6.76 (dd, 1H), 2.14 (m, 1H), 1.94 (m, 1H), 1.64 (s, 3H), 0.99 (t, 3H). LC-MS: m/e 196 (M+H)$^+$ (1.8 min).

REFERENCE EXAMPLE 14

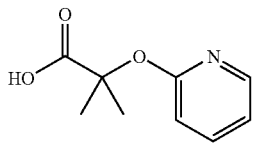

2-(2-Pyridyloxy)-2-methylpropionic Acid

The title compound was prepared following the procedures described for Reference Example 13 substituting ethyl iodide and sodium hexamethyldisilazide with methyl iodide and potassium hexamethyldisilazide respectively at Step B.

$^1$H NMR (500 MHz, CD$_3$OD): δ 8.04 (dd, 1H), 7.64 (ddd, 1H), 6.89 (dd, 1H), 6.76 (dd, 1H), 1.66 (s, 6H). LC-MS: m/e 182 (M+H)$^+$ (1.5 min).

REFERENCE EXAMPLE 15

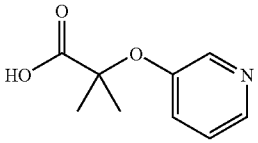

2-(3-Pyridyloxy)-2-methylpropionic Acid

The title compound was prepared following the procedures described for Reference Example 14 substituting 2-hydroxypyridine with 3-hydroxypyridine at Step A and ethyl iodide with methyl iodide at Step B. $^1$H NMR (500 MHz, CD$_3$OD): δ 8.21 (d, 1H), 8.19 (dd, 1H), 7.43-7.35 (m, 2H), 1.62 (s, 6H). LC-MS: m/e 182 (M+H)$^+$ (0.3 min).

REFERENCE EXAMPLE 16

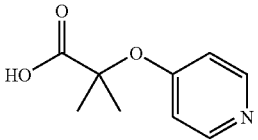

2-(4-Pyridyloxy)-2-methylpropionic Acid

Step A: N-Trimethylsilylethoxymethyl-4-pyridone.

To a solution of 4-hydroxypyridine (3.0 g, 32 mmol) and trimethylsilylethoxymethyl chloride (5.5 mL, 32 mmol) in 30 mL of acetonitrile was added cesium carbonate (11 g, 34 mmol). After stirring at room temperature overnight, the reaction mixture was partitioned between brine (100 mL) and ethyl acetate (100 mL). The organic layer was separated and aqueous layer extracted with ethyl acetate (3×100 mL). The combined extracts were dried over anhydrous sodium sulfate, filtered, and concentrated to dryness to give the title compound contaminated with some O-alkylated product. $^1$H NMR (500 MHz, CD$_3$OD): δ 7.92 (d, 2H), 6.49 (d, 2H), 5.28 (s, 2H), 3.62 (t, 2H), 0.96 (t, 2H), 0.024 (s, 9H).

Step B: Benzyl 2-(4-Pyridyloxy)propionate

To a solution of benzyl lactate (6.0 g, 33 mmol) and N-methyl morpholine (2.7 mL, 33 mmol) in 100 mL of anhydrous methylene chloride at −20° C. was added trifluoromethanesulfonyl anhydride (5.6 mL, 33 mmol). After stirring at −20° C. for 1 h, the reaction mixture was diluted with 100 mL of hexane and washed with dilute aqueous sodium hydrogen sulfate and brine/saturated aqueous sodium bicarbonate. The organic layer was separated, dried over anhydrous magnesium sulfate, filtered, and concentrated to dryness, and the residue was purified by flash column chromatography on silica gel eluted with 10% ether in hexane to give benzyl 2-trifluoromethanesulfonyloxypropionate (6.4 g), which was used immediately for the ensuing reaction. Thus, a mixture of N-trimethylsilylethoxymethyl-4-pyridone (Step A, 3.4 g, 15 mmol) and benzyl 2-trifluromethanesulfonyloxypropionate (4.7 g, 15 mmol) was heated at 60° C. overnight. After cooling to room temperature, the reaction mixture was dissolved in methylene chloride and loaded onto a silica gel column, which was eluted with 5% methanol in methylene chloride to give the title compound. $^1$H NMR (500 MHz, CD$_3$)D): δ 8.57 (d, 2H), 7.42 (d, 2H), 7.4-7.3 (m, 5H), 5.44 (q, 1H), 5.24 (ABq, 2H), 1.72 (d, 3H). LC-MS: m/e 258 (M+H)$^+$ (1.8 min).

Step C: 2-(4-Pyridyloxy)-2-methylpropionic Acid.

The product of Step B (4.5 g, 18 mmol) was converted to the title compound following the procedure described on Reference Example 13, Steps B-C substituting benzyl 2-(2-pyridyloxy)propionate and ethyl iodide with benzyl 2-(4-pyridyloxy)propionate and methyl iodide at Step B. $^1$H NMR (500 MHz, CD$_3$OD): δ 8.44 (d, 2H), 7.14 (d, 2H), 1.70 (s, 6H). LC-MS: m/e 18(M+H)$^+$ (0.28 min).

REFERENCE EXAMPLE 17

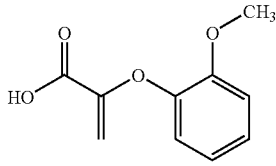

2-(2-Methoxyphenyloxy)propenoic Acid

Step A: Methyl 2-(2-Methoxyphenyloxy)propenoate.

To a solution of 2,3-dihydro-1,4-benzodioxine-2-carboxylic acid (1.0 g, 5.6 mmol) in methylene chloride (10 mL) and methanol (10 mL) at 0° C. was added trimethylsilyidiazomethane (2 M in hexane) until yellow color persisted, and the reaction was stirred at room temperature for 15 min. The reaction mixture was concentrated to dryness and azeotroped with toluene. The residue was dissolved in anhydrous tetrahydrofuran (20 mL), and was added methyl iodide (1.8 mL, 28 mmol) and potassium hexamethyidisilazide (0.5 M in toluene, 17 mL, 8.5 mmol) at −78° C. The reaction was allowed to warm to room temperature over 4 h, diluted with ethyl acetate (100 mL), washed with saturated ammonium chloride (100 mL) and water (100 mL), dried over anhydrous sodium sulfate, filtered, and concentrated to dryness to give the title compound. $^1$H NMR (500 MHz, CD$_3$OD): δ 7.07 (ddd, 1H), 6.97 (dd, 1H), 6.94 (dd, 1H), 6.85 (ddd, 1H), 5.52 (d, 1H), 4.64 (d, 1H), 3.86 (s, 3H), 3.83 (s, 3H). LC-MS: m/e 231 (M+Na)$^+$ (2.6 min).

Step B: 2-(2-Methoxyphenyloxy)propenoic Acid.

To a solution of methyl 2-(2-methoxyphenyloxy)propenoate (0.30 g, 1.4 mmol) in tetrahydrofuran (30 mL) and water (30 mL) was added lithium hydroxide monohydrate 0.17 g, 4.0 mmol). After stirring at room temperature overnight, the reaction was quenched by addition of concentrated hydrochloric acid (final pH=2), and the product was extracted with ethyl acetate (3×100 mL). The combined extracts were dried over anhydrous sodium sulfate, filtered, and concentrated to dryness to give the title compound. $^1$H NMR (500 MHz, CD$_3$OD): δ 7.42 (ddd, 1H), 7.22 (dd, 1H), 7.10 (dd, 1H), 6.97 (ddd, 1H), 5.48 (d, 1H), 4.51 (d, 1H), 3.64 (s, 3H).

REFERENCE EXAMPLE 18

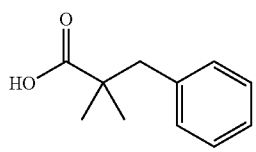

2,2-Dimethyl-3-phenylpropionic Acid

Step A: 1-Phenyl-2-chloro-2-methylpropane.

A mixture of 5.92 g (40 mmol) of 1-phenyl-2-hydroxy-2-methylpropane and 50 mL of conc. hydrochloric acid was stirred at ice bath temperature for 1 h and at RT for 3 h. The reaction mixture was then extracted with ether. The organic layer was dried over MgSO4. Solvent removal gave 1-phenyl-2-chloro-2-methylpropane.

Step B: 2,2-Dimethyl-3-phenylpropionic Acid.

A mixture of 3.36 g (20 mmol) of the above chloride, and 560 mg (23 mmol) of magnesium turnings in 20 mL of THF containing 0.01 mL of 1,2-dibromoethane was stirred for 4 h at RT. Most of the metal was digested. Carbon dioxide from dry ice in a flask connected with a hose was bubbled for 3 h. The reaction mixture was then stirred overnight at RT and quenched with 1N HCl. This was then extracted with EtOAc. The organic phase was dried over MgSO$_4$. Solvent removal gave a residue, which was partitioned between ether and 2N NaOH. The aqueous layer was washed with ether then acidified with 2N HCl and extracted with EtOAc. The EtOAc solution was dried over MgSO$_4$. The solvent was removed in vacuo to give the desired 2,2-dimethyl-3-propionic acid as an oil. NMR: 1.22 (s; 6H), 2.9 (s, 2H), 7.15-7.34 (m, 5H).

REFERENCE EXAMPLE 19

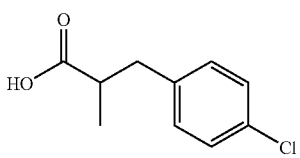

2-Methyl-3-(4-chlorophenyl)propionic Acid

A solution of 3-(4-chlorophenyl)propionic acid (1.85 g, 10 mmol) in 10 mL of THF was added to 16 mL of freshly prepared 1.5 M LDA (24 mmol) at dry ice-acetone bath temp. The reaction mixture was stirred 1 hr as it warmed to −30° C. and 1.6 mL (25 mmol) of methyl iodide was added. The resulting mixture was stirred at the same temp. for 0.5 h and the stirring was continued at RT overnight. The reaction was quenched with 1 N HCl, and diluted with ether. The solution was washed with water, 10% sodium thiosulfate and brine. The organic layer was dried over MgSO$_4$. Solvent removal gave a mixture of the desired methylated product and the starting acid. Repetition of the above procedure on this residue gave the desired 2-methyl-3-(4-chlorophenyl) propionic acid contaminated with ~5% of the starting acid as an oil. NMR: 1.5 (d, 3H), 4.78 (q, 1H). 6.84 & 7.26 (2d, 4H).

REFERENCE EXAMPLE 20

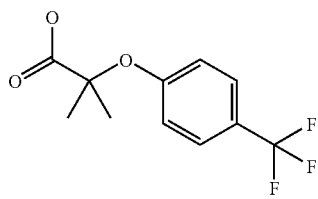

2-Methyl-2-(4-trifluoromethylphenyloxy)propionic Acid

The title compound was prepared following the same procedure described for Reference Example 1. $^1$H NMR (500 MHz, CD$_3$OD): δ 7.56 (d, 2H), 7.00 (d, 2H), 1.62 (s, 6H).

REFERENCE EXAMPLE 21

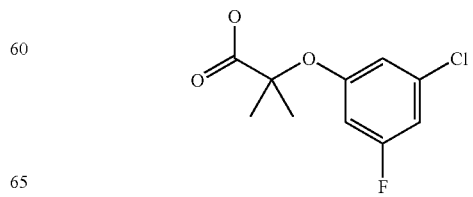

2-Methyl-2-(3-chloro-5-fluorophenyloxy)propionic Acid

Step A: 3-Chloro-5-fluorophenol

To a solution of 1-bromo-3-chloro-5-fluorobenzene (16 g, 76 mmol) in 250 mL of anhydrous ether at −78° C. was added tert-butyllithium (1.7 M, 100 mL, 170 mmol). After stirring at −78° C. for 1 h, trimethyl borate (20 mL, 176 mmol) was added, and the reaction was allowed to warm to room temperature overnight. The resulting mixture was cooled to −10° C., and was added peracetic acid (32% in acetic acid, 35 mL). After stirring at 0° C. for 30 min, potassium bisulfite (5 g) was added. After stirring at room temperature for 30 min, the aqueous layer was separated and the organic mixture was extracted with 3 M aqueous sodium hydroxide (3×100 mL). The aqueous extracts were acidified with concentrated hydrochloric acid (pH=2), and was extracted with ether (3×150 mL). The combined ether extracts were dried over anhydrous magnesium sulfate, filtered and concentrated to afford the crude phenol, which was azeotroped with heptane (100 mL) to remove traces of acetic acid to give the title compound. $^1$H NMR (500 MHz, CD$_3$OD): δ 7.51 (br s, 1H), 7.35 (br d, 1H), 7.21 (m, 1H).

Step B: 2-Methyl-2-(3-chloro-5-fluorophenyloxy)propionic Acid

The title compound was prepared following the procedures described for Reference Example 1. $^1$H NMR (500 MHz, CD$_3$OD): δ 7.53 (br s, 1H), 7.36 (br d, 1H), 7.20 (m, 1H), 1.24 (s, 6H).

REFERENCE EXAMPLE 22

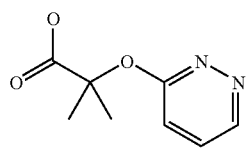

2-Methyl-2-(3-pyridazinyloxy)propionic Acid

The title compound was prepared following the procedures described for Reference Example 13 substituting 2-hydroxypyridine with 3-hydroxypyridazine at Step A and ethyl iodide with methyl iodide at Step B. $^1$H NMR (500 MHz, CD$_3$OD): δ 7.98 (dd, 1H), 7.45 (dd, 1H), 6.96 (dd, 1H), 1.70 (s, 6H).

REFERENCE EXAMPLE 23

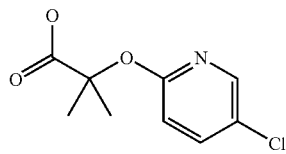

2-Methyl-2-(5-chloro-2-pyridyloxy)propionic Acid

Step A: Ethyl 2-Methyl-2-(5-chloro-2-pyridyloxy)propionate

A mixture of 5-chloro-2-hydroxypyridine (5.0 g, 39 mmol), ethyl 2-bromoisobutyrate (5.7 mL, 39 mmol) and cesium carbonate (25 g, 77 mmol) in 50 mL of acetonitrile was heated at 50° C. overnight. The volatile materials were removed by concentrating on a rotary evaporator, and the residue was partitioned between water (100 mL) and ethyl acetate (100 mL). The organic layer was separated and the aqueous layer extracted with ethyl acetate (2×100 mL). The combined organic extracts were dried over anhydrous sodium sulfate, filtered and concentrated to dryness, and the residue was purified by flash column chromatography on silica gel eluted with 5% ethyl acetate in hexane to give the title compound. $^1$H NMR (500 MHz, CD$_3$OD): δ 7.99 (d, 1H), 7.67 (dd, 1H), 6.68 (d, 1H), 4.13 (q, 2H), 1.64 (s, 6H), 1.14 (t, 3H). LC-MS: m/e 244 (M+H)$^+$ (3.41 min).

Step B: 2-Methyl-2-(5-chloro-2-pyridyloxy)propionic Acid

A mixture of ethyl 2-methyl-2-(5-chloro-2-pyridyloxy) propionate and sodium hydroxide (0.85 g, 21 mmol) in 15 mL of acetonitrile and 15 mL of water was heated at 50° C. overnight. The volatile materials were removed by concentrating on a rotary evaporator, and the residue was partitioned between 2 M hydrochloric acid (100 mL) and ether (100 mL). The organic layer was separated and washed with water (2×50 mL), dried over anhydrous magnesium sulfate, filtered and concentrated to dryness to give the title compound. $^1$H NMR (500 MHz, CD$_3$OD): δ 8.02 (d, 1H), 7.65 (dd, 1H), 6.77 (d, 1H), 1.62 (s, 6H). LC-MS: m/e 216 (M+H)$^+$ (2.33 min).

REFERENCE EXAMPLE 24

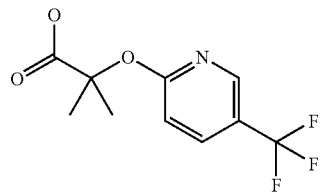

2-Methyl-2-(5-trifluoromethyl-2-pyridyloxy)propionic Acid

The title compound was prepared following the procedures described for Reference Example 23 substituting 5-chloro-2-hydroxpyridine with 5-trifluoromethyl-2-hydroxypyridine at Step A. $^1$H NMR (500 MHz, CD$_3$OD): δ 8.38 (br s, 1H), 7.93 (dd, 1H), 7.13 (d, 1H), 1.70 (s, 6H). LC-MS: m/e 250 (M+H)$^+$ (2.6 min).

REFERENCE EXAMPLE 25

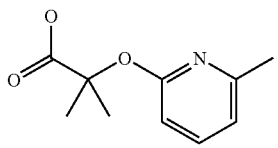

2-Methyl-2-(6-methyl-2-pyridyloxy)propionic Acid

The title compound was prepared following the procedures described for Reference Example 23 substituting 5-chloro-2-hydroxpyridine with 6-methyl-2-hydroxpyridine at Step A. $^1$H NMR (500 MHz, CD$_3$OD): δ 7.51 (t, 1H), 6.74 (d, 1H), 6.53 (d, 1H), 2.34 (s, 3H), 1.64 (s, 6H). LC-MS: m/e 196 (M+H)$^+$ (1.3 min).

REFERENCE EXAMPLE 26

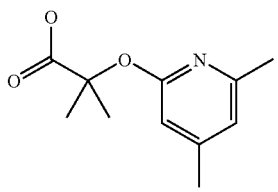

2-Methyl-2-(4,6-dimethyl-2-pyridyloxy)propionic Acid

The title compound was prepared following the procedures described for Reference Example 23 substituting 5-chloro-2-hydroxpyridine with 4,6-dimethyl-2-hydroxpyridine at Step A. LC-MS: m/e 210 (M+H)$^+$ (1.17 min).

REFERENCE EXAMPLE 27

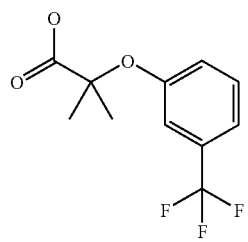

2-Methyl-2-(3-trifluoromethylphenyloxy)propionic Acid

The title compound was prepared following the same procedure described for Reference Example 1. $^1$H NMR (500 MHz, CD$_3$OD): δ 7.45 (t, 1H), 7.28 (d, 1H), 7.16 (s, 1H), 7.13 (d, 1H), 1.62 (s, 6H).

REFERENCE EXAMPLE 28

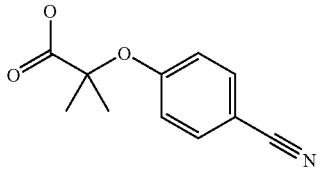

2-Methyl-2-(3-cyanophenyloxy)propionic Acid

The title compound was prepared following the same procedure described for Reference Example 1. $^1$H NMR (500 MHz, CD$_3$OD): δ 7.63 (d, 2H), 6.97 (d, 2H), 1.65 (s, 6H).

REFERENCE EXAMPLE 29

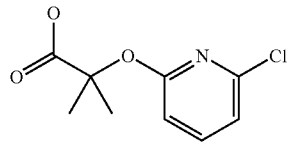

2-Methyl-2-(6-chloromethyl-2-pyridyloxy)propionic Acid

The title compound was prepared following the procedures described for Reference Example 23 substituting 5-chloro-2-hydroxpyridine with 6-chloro-2-hydroxpyridine at Step A. $^1$H NMR (500 MHz, CD$_3$OD): δ 7.64 (t, 1H), 6.95 (d, 1H), 6.72 (d, 1H), 1.65 (s, 6H). LC-MS: m/e 216 (M+H)$^+$ (2.4 min).

REFERENCE EXAMPLE 30

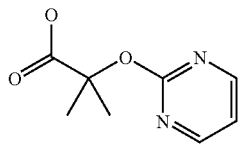

2-Methyl-2-(2-pyrimidyloxy)propionic Acid

The title compound was prepared following the procedures described for Reference Example 23 substituting 5-chloro-2- hydroxpyridine with 2-hydroxpyrimidine at Step A. ¹H NMR (500 MHz, CD₃OD): δ 8.53 (d, 2H), 7.09 (t, 1H), 1.74 (s, 6H).

REFERENCE EXAMPLE 31

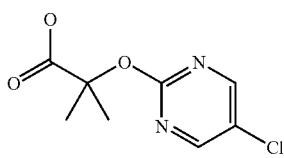

2-Methyl-2-(5-chloro-2-pyrimidyloxy)propionic Acid

The title compound was prepared following the procedures described for Reference Example 23 substituting 5-chloro-2-hydroxpyridine with 5-chloro-2-hydroxpyrimidine at Step A. ¹H NMR (500 MHz, CD₃OD): δ 8.55 (s, 2H), 1.73 (s, 6H).

REFERENCE EXAMPLE 32

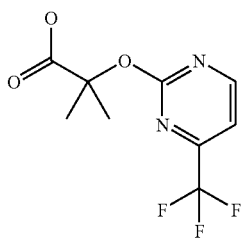

2-Methyl-2-(4-trifluoromethyl-2-pyrimidyloxy)propionic Acid

The title compound was prepared following the procedures described for Reference Example 23 substituting 5-chloro-2-hydroxpyridine with 4-trifluoromethyl-2-hydroxpyrimidine at Step A. ¹H NMR (500 MHz, CD₃OD): δ 8.85 (d, 1H), 7.48 (d, 1H), 1.76 (s, 6H).

REFERENCE EXAMPLE 33

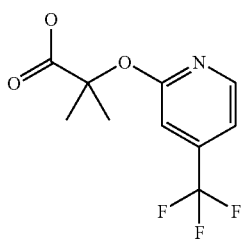

2-Methyl-2-(4-trifluoromethyl-2-pyridyloxy)propionic Acid

The title compound was prepared following the procedures described for Reference Example 23 substituting 5-chloro-2-hydroxpyridine with 4-trifluoromethyl-2-hydroxpyridine at Step A. ¹H NMR (500 MHz, CD₃OD): δ 8.30 (d, 1H), 7.18 (d, 1H), 7.05 (s, 1H), 1.71 (s, 6H).

REFERENCE EXAMPLE 34

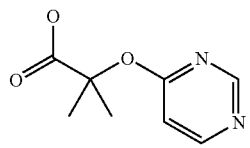

2-Methyl-2-(4-pyrimidyloxy)propionic Acid

The title compound was prepared following the procedures described for Reference Example 23 substituting 5-chloro-2-hydroxpyridine with 4-hydroxpyrimidine at Step A. ¹H NMR (500 MHz, CD₃OD): δ 8.67 (s, 1H), 8.47 (d, 1H), 6.91 (d, 1H), 1.73 (s, 6H).

REFERENCE EXAMPLE 35

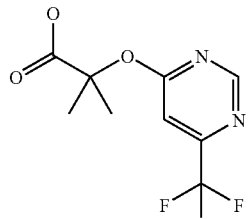

2-Methyl-2-(6-trifluoromethyl-4-pyrimidyloxy)propionic Acid

The title compound was prepared following the procedures described for Reference Example 23 substituting 5-chloro-2-hydroxpyridine with 6-trifluoromethyl-4-hydroxpyrimidine at Step A. ¹H NMR (500 MHz, CD₃OD): δ 8.81 (s, 1H), 7.28 (s, 1H), 1.75 (s, 6H). LC-MS: m/e 251 (M+H)⁺ (2.1 min).

REFERENCE EXAMPLE 36

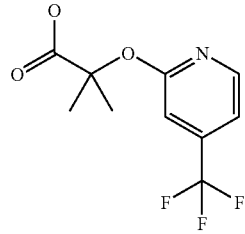

2-Methyl-2-(4-trifluoromethyl-2-pyridyloxy)propionic Acid

Step A: 2-(4-Trifluoromethyl-2-pyridyloxy)propionic Acid

To a suspension of lithium lactate (7.8 g, 81 mmol) in 100 mL of anhydrous dimethylformamide was added sodium hydride (60% dispersion in mineral oil, 3.2 g, 80 mmol). After stirring at room temperature for 30 min, 2-chloro-4-trifluromethylpyridine (10 g, 55 mmol) was added, and the mixture was heated at 100° C. overnight. The reaction was cooled to room temperature, poured into 500 mL of water, and was washed with hexane (200 mL). The aqueous solution was acidified with concentrated hydrochloric acid (pH>2), and was extracted with ether (2×500 mL). The combined extracts were washed with water and brine, dried over anhydrous sodium sulfate, filtered and concentrated to dryness to give the title compound.

Step B: Methyl 2-Methyl-2-(4-trifluoromethyl-2-pyridyloxy)propionate

To a solution of 2-(4-trifluoromethyl-2-pyridyloxy)propionic acid (Step A, 15 g, 55 mol) in 100 mL of methylene chloride and 100 mL of methanol at 0° C. was added trimethylsilyldiazomethane (2 M solution in hexane) until a yellow color persisted. After stirring at room temperature for 15 min, the reaction mixture was concentrated to dryness, and the residue was purified by flash chromatography on silica gel eluted with 0 to 10% ethyl acetate in hexane to give methyl 2-(4-trifluoromethyl-2-pyridyloxy)propionate, which was used immediately for methylation following the procedure described in Reference Example 13, Step B substituting ethyl iodide with methyl iodide. $^1$H NMR (500 MHz, CD$_3$OD): δ 8.25 (d, 1H), 7.18 (d, 1H), 7.15 (s, 1H), 3.65 (s, 3H), 1.65 (s, 6H).

Step C: 2-Methyl-2-(4-trifluoromethyl-2-pyridyloxy)propionic Acid

To a solution of methyl 2-methyl-2-(4-trifluoromethyl-2-pyridyloxy)propionate (Step B, 7.5 g, 29 mol) in 50 mL of methanol, 50 mL of tetrahydrofuran and 50 mL of water was added sodium hydroxide (2.3 g, 57 mmol). After stirring at 50° C. for 5 h, the reaction mixture was partially concentrated, and was added 2 M hydrochloric acid to pH >2. The resulting mixture was extracted with ethyl acetate (2×200 mL), and the combined extracts were dried over anhydrous sodium sulfate, filtered, and concentrated to dryness to afford the title compound. $^1$H NMR (500 MHz, CD$_3$OD): δ 8.28 (d, 1H), 7.17 (d, 1H), 7.05 (s, 1H), 1.70 (s, 6H).

REFERENCE EXAMPLE 37

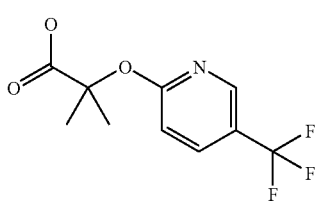

2-Methyl-2-(5-trifluoromethyl-2-pyridyloxy)propionic Acid

The title compound was prepared following the procedure described in Reference Example 36, Step A with 1.5 extra equivalent of sodium hydride substituting lithium lactate with hydroxyisobutyric acid and 2-chloro-4-trifluoromethylpyridine 2-chloro-5-trifluoromethylpyridine. $^1$H NMR (500 MHz, CD$_3$OD): δ 8.38 (br, 1H), 7.94 (dd, 1H), 6.93 (d, 1H), 1.69 (s, 6H).

REFERENCE EXAMPLE 38

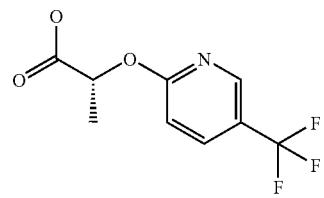

2(R)-(5-Trifluoromethyl-2-pyridyloxy)propionic Acid

Step A: 2(R)-(5-trifluoromethyl-2-pyridyloxy)propionate

The title compound was prepared following the procedure described in Reference Example 14, Step A substituting 2-hydroxypyridine with 5-trifluoromethyl-2-hydroxypyridine and benzyl lactate with benzyl (S)-lactate. LC-MS: m/e 326 (M+H)$^+$ (3.1 min).

Step B: 2(R)-(5-trifluoromethyl-2-pyridyloxy)propionic Acid

The title compound was prepared following the procedure described in Reference Example 13, Step C substituting benzyl 2-(2-pyridyloxy)-2-methylbutanoate with 2(R)-(5-trifluoromethyl-2-pyridyloxy)propionate (Step A). $^1$H NMR (500 MHz, CD$_3$OD): δ 8.70 (s, 1H), 7.67 (d, 1H), 6.63 (d, 1H), 5.30 (q, 1H), 1.67 (d, 3H).

REFERENCE EXAMPLE 39

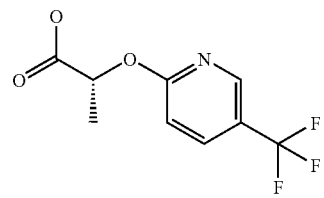

2(R)-(5-Trifluoromethyl-2-pyridyloxy)propionic Acid

Step A 2(R)-(5-trifluoromethyl-2-pyridyloxy)propionate

The title compound was prepared following the procedure described in Reference Example 13, Step A substituting 2-hydroxypyridine with 5-trifluoromethyl-2-hydroxypyridine and benzyl lactate with benzyl (S)-lactate. LC-MS: m/e 326 (M+H)$^+$ (3.1 min).

Step B 2(R)-(5-trifluoromethyl-2-pyridyloxy)propionic Acid

The title compound was prepared following the procedure described in Reference Example 13, Step C substituting benzyl 2-(2-pyridyloxy)-2-methylbutanoate with 2(R)-(5-trifluoromethyl-2-pyridyloxy)propionate (Step A). $^1$H NMR (500 MHz, CD$_3$OD): δ 8.70 (s, 1H), 7.67 (d, 1H), 6.63 (d, 1H), 5.30 (q, 1H), 1.67 (d, 3H).

REFERENCE EXAMPLE 40

2-Methyl-2-(5-trifluoromethyl-2-pyridyloxy)propionic Acid

Two nitrogen flushed, 12 L 3-necked round bottom flasks, each fitted with a thermometer and a reflux condenser were charged with KHMDS in THF (0.91 M, 3.52 L each, 3.205 mol, 1.5 eq). The solutions were cooled to −70° C. and stirred magnetically. Ethyl-2-hydroxyisobutyrate (98%) (463 mL, 447g, 3.38 mol) was added to each flask over 30 min, keeping the reaction temperature below −62° C. After 10 min 2-chloro-5-trifluormethylpyridine (388 g, 2.14 mol) was added to each flask in one portion. The cooling bath was removed and the reactions were allowed to warm to 20° C. overnight (ca 16 hr.). The reactions were monitored by TLC (silica, 90/10 Hex/EtOAc) and HPLC:

Sodium hydroxide (1.36 L, 5N) was added to each reaction flask and the reactions were refluxed overnight (ca 22 hr). The reactions were concentrated together on a rotary evaporator to remove the THF. To the concentrate was added water (4L) and the solution extracted with n-heptane (2×4 L). The aqueous layer was added over 10 min to 2N HCl (9 L, 18 mol) with stirring. The resulting suspension was aged for 30 min (temperature 30° C.) then filtered. The cake was washed with water (3×2 L), and air-dried to a damp tan solid.

The material was dissolved in n-heptane (4 L) at 65° C. IPAc (1 L) and DARCO KB (40 g, 100 mesh) were added. The mixture was stirrer for 15 min, filtered through CELITE diatomaceous earth, and the cake washed with 4:1 heptane/IPAc (3×500 mL). The filtrate was concentrated to ca. 2 L affording a white suspension. The slurry was flushed with heptane (2×3 L) and concentrated to ca. 3 L. The resulting white suspension was cooled to 0° C. and aged 1 hr. The product was filtered and the cake washed with cold heptane (1 L) to provide the title compound as white crystalline material. HPLC Column: YMC Combiscreen Pro C18, 50×4.6 mm; Mobile phase: A 0.1% TFA in H$_2$O; B CH$_3$CN. Gradient: 90/10 A/B to 10/90 A/B in 4 min. Flow rate: 4 mL/min. Detection: 254 nm. R$_t$ 2-chloro-5-trifluormethylpyridine 2.1 min. R$_t$ 2-ethoxy-5-trifluoromethylpyridine 2.9 min. R$_t$ Product Ester 3.1 min. R$_t$ Final Acid 2.05 min

REFERENCE EXAMPLE 41

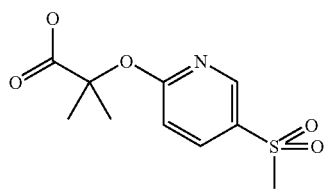

2-Methyl-2-(5-methylsulfonyl-2-pyridyloxy)propionic Acid

Step A Ethyl 2-(5-Methylsulfonyl-2-pyridyloxy)propionate

A mixture of ethyl 2-hydroxyisobutyrate (0.41 mL, 3.0 mmol), 2,5-bis(methyl sulfonyl) pyridine (J. Heterocycl. Chem. 1985, 22, 1583) (0.70 g, 3.0 mmol) and sodium hydride (60% dispersion in mineral oil, 0.14 g, 3.6 mmol) in 30 mL of anhydrous DMF was heated at 80° C. overnight. The reaction mixture was cooled to room temperature, and was partitioned between saturated aqueous ammonium chloride (200 mL) and ether (200 mL). The organic layer was separated and was washed with water and brine, dried over anhydrous sodium sulfate, filtered and concentrated to dryness, and the residue was purified by flash column chromatography on silica gel eluting with 0 to 80% ethyl acetate in hexane to give the title compound as a 1:1 mixture with 2-ethoxy-5-methylsulfonylpyridine. LC-MS: m/e 288 (M+H)$^+$ (0.70 min).

Step B 2-Methyl-2-(5-methylsulfonyl-2-pyridyloxy)propionic Acid

To a solution of ethyl 2-methyl-2-(5-methylsulfonyl-2-pyridyloxy)propionate (Step A, 0.45 g, 1.6 mol) in 5 mL MeOH, 10 mL THF and 10 mL water was added sodium hydroxide (0.19 g, 4.7 mmol). After stirring at room temperature for 3 days, the reaction mixture was partially concentrated, and was added 2 M hydrochloric acid to pH>2. The resulting mixture was extracted with EtOAc (2×20 mL), and the combined extracts were dried over anhydrous sodium sulfate, filtered, and concentrated to dryness to afford the title compound. $^1$H NMR (500 MHz, CD$_3$OD): δ 8.60 (d, 1H), 8.16 (dd, 1H), 7.17 (d, 1H), 3.15 (s, 3H), 1.71 (s, 6H).

REFERENCE EXAMPLE 42

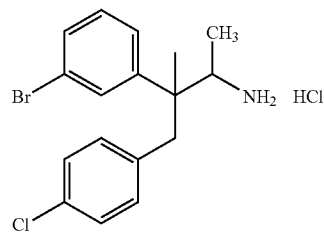

N-{[2-(3-Bromophenyl)-3-(4-chlorophenyl)-1,2-dimethyl]propyl}amine, hydrochloride (Diastereomer α and β)

Step A: 1-(3-bromophenyl)acetone

To a solution of N-methoxy-N-methylacetamide (10 g, 0.10 mol) in 200 mL of ether at 0° C. was added 3-bromobenzylmagnesium bromide (0.25 M, 200 mL, 50 mmol). After stirring at 0° C. for 2 h, the reaction mixture was partitioned between hexane and saturated aqueous ammonium chloride. The organic layer was separated, washed with brine, dried over anhydrous magnesium sulfate, filtered and concentrated to dryness to give the title compound, which was used without further purification. $^1$H NMR (500 MHz, CD$_3$OD): δ 7.5-7.1 (m, 4H), 3.78 (s, 2H), 2.19 (s, 3H).

Step B: 3-(3-Bromophenyl)-2-butanone

To a solution of 3-bromophenylacetone (4.7 g, 22 mmol) in acetonitrile (100 mL) was added methyl iodide (1.4 mL, 22 mmol) and cesium carbonate (14 g, 44 mmol). After stirring at room temperature for 17 h, the reaction mixture was poured into ether (100 mL) and water (100 mL). The organic layer was separated and the aqueous layer extracted with ether. The combined organic extracts were dried over magnesium sulfate, filtered, and concentrated to dryness to give the title compound. $^1$H NMR (400 MHz, CD$_3$OD): δ 7.45-7.40 (m, 2H), 7.3-7.2 (m, 2H), 3.87 (q, 1H), 2.06 (s, 3H), 1.34 (d, 3H).

Step C: 3-(3-Bromophenyl)-4-(4-chlorophenyl)-3-methyl-2-butanone

To a solution of 3-(3-bromophenyl)-2-butanone (2.0 g, 8.8 mmol) in methylene chloride (100 mL) was added 4-chlorobenzyl chloride (1.4 g, 8.8 mmol), tetrabutylammonium iodide (0.16 g, 0.44 mmol) and cesium hydroxide monohydrate (5.9 g, 35 mmol). After stirring at room temperature for 3.5 h, the reaction mixture was poured into ethyl acetate (100 mL) and water (100 mL). The organic layer was separated and the aqueous layer extracted with ethyl acetate. The combined organic extracts were washed with brine, dried over magnesium sulfate, filtered, and concentrated to dryness to give the title compound. $^1$H NMR (400 MHz, CD$_3$OD): δ 7.5-7.1 (m, 4 H), 7.08 (d, 2H), 6.68 (d, 2H), 3.16 (ABq, 2H), 1.98 (s, 3H), 1.42 (s, 3H).

Step D: 3-(3-Bromophenyl)-4-(4-chlorophenyl)-3-methyl-2-butanol

To a solution of 3-(3-bromophenyl)-4-(4-chlorophenyl)-3-methyl-2-butanone (1.6 g, 4.6 mmol) in methanol (50 mL) was added sodium borohydride (0.26 g, 6.8 mmol). After stirring at room temperature for 10 min, the reaction was quenched by addition of saturated aqueous ammonium chloride (25 mL). The precipitate was filtered off and washed with ethyl acetate (25 mL). The organic layer of the filtrate was separated, washed with brine, dried over anhydrous sodium sulfate, filtered and concentrated to dryness. The residue was purified by flash column chromatography on silica gel eluted with 5% ethyl acetate in hexane to afford the title compound as two separate diastereomers. Faster eluting diastereomer (Diastereomer α) $^1$H NMR (400 MHz, CD$_3$OD): δ 7.63 (s, 1H), 7.42-7.18 (m, 3H), 7.05 (d, 2H), 6.80 (d, 2H), 3.92 (q, 1H), 3.19 (d, 1H), 2.86 (d, 1H), 1.13 (s, 3H), 1.02 (d, 3H). Slower eluting diastereomer (Diastereomer β) $^1$H NMR (400 MHz, CD$_3$OD): 7.40-7.18 (m, 4H), 7.04 (d, 2H), 6.64 (d, 2H), 4.12 (q, 1H), 3.04 (ABq, 2H), 1.17 (s, 3H), 0.84 (d, 3H).

Step E: 2-Azido-3-(3-bromophenyl)-4-(4-chlorophenyl)-3-methylbutane

To a solution of 3-(3-bromophenyl)-4-(4-chlorophenyl)-3-methyl-2-butanol (fasting eluting diastereomer, 0.90 g, 2.5 mmol) in ethyl acetate (80 mL) at 0° C. was added triethyl amine (dried over activated molecular sieves, 0.42 mL. 3.1 mmol) and methanesulfonyl chloride (0.22 mL, 2.8 mmol). After stirring at 0° C. for 2 h, the reaction was quenched by addition of saturated aqueous sodium bicarbonate (10 mL). After stirring at room temperature for 0.5 h, the organic layer was separated, washed with brine, dried over anhydrous magnesium sulfate, filtered, and concentrated to dryness to give the crude sulfonate, which was used without further purification. Thus, a mixture of the sulfonate and sodium azide (0.83 g, 0.13 mol) in dimethylformamide (5 mL) was heated at 120° C. for 4 h. The reaction mixture was cooled to room temperature and was poured into water (40 mL), and the product was extracted with ether (2×20 mL). The combined organic extracts were washed with water, dried over magnesium sulfate, filtered and concentrated to dryness, and the residue was purified on a silica gel column eluting with hexane to give the title compound (Diastereomer α). $^1$H NMR (400 MHz, CD$_3$OD): δ 7.43-7.20 (m, 4H), 7.04 (d, 2H), 6.64 (d, 2H), 4.10 (q, 1H), 3.10 (d, 1H), 3.00 (d, 1H), 1.10 (s, 3H), 1.02 (d, 3H).

The slower eluting diastereomer was converted to the other diastereomer (Diastereomer β) of the title compound following the same procedure as described for the faster eluting diastereomer. $^1$H NMR (400 MHz, CD$_3$OD): δ 7.60-7.20 (m, 4H), 7.07 (d, 2H), 6.80 (d, 2H), 3.90 (q, 1H), 3.17 (d, 1H), 2.92 (d, 1H), 1.22 (d, 3H), 1.20 (s, 3H).

Step F: 2-(N-tert-Butoxycarbonyl)amino-3-(3-bromophenyl)-4-(4-chlorophenyl)-3-methylbutane To a solution of 2-azido-3-(3-bromophenyl)-4-(4-chlorophenyl)-3-methylbutane (Diastereomer α, 0.26 g, 0.68 mmol) in ethyl acetate (5 mL) was added di(tert-butyl)dicarbonate (0.18 g, 0.82 mmol) and platinum dioxide (0.025 g). The mixture was degassed and charged with hydrogen with a balloon. After stirring for 1 day, the reaction mixture was filtered through CELITE, diatomaceous earth, and the filtrate was concentrated to give diastereomer a of the title compound.

Diastereomer β of 2-azido-3-(3-bromophenyl)-4-(4-chlorophenyl)-3-methylbutane was converted to the Diastereomer β of the title compound following the same procedure as described for Diastereomer α.

Step G: N-[3-(4-Chlorophenyl)-2-(3-bromophenyl)-1,2-dimethylpropyl]-amine hydrochloride (Diastereomer α and β)

2-(N-tert-Butoxycarbonyl)amino-3-(3-bromophenyl)-4-(4-chlorophenyl)-3-methylbutane (Diastereomer α, 0.35 g, 0.76 mmol) was treated with 4 M hydrogen chloride in dioxane (5 mL) at room temperature for 2 h. The mixture was concentrated to dryness to give Diastereomer a of the title compound. LC-MS: m/e 352 (M+H)$^+$ (3.0 min).

Diastereomer β of 2-azido-3-(3-bromophenyl)-4-(4-chlorophenyl)-3-methylbutane was converted to Diastereomer β of the title compound following the same procedure as described for Diastereomer α. LC-MS: m/e 352 (M+H)$^+$ (3.0 min).

REFERENCE EXAMPLE 43

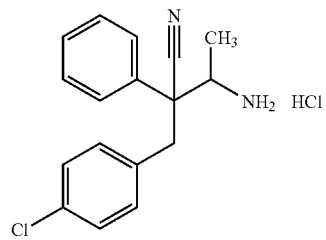

N-{[3-(4-Chlorophenyl)-2-phenyl-2-cyano-1-methyl]propyl}amine, hydrochloride

Step A: 4-(4-Chlorophenyl)-3-cyano-3-phenyl-2-butanone.

To a solution of α-acetylphenylacetonitrile (1.0 g, 6.3 mmol) in acetonitrile (25 mL) was added 4-chlorobenzyl bromide (1.3 g, 6.3 mmol) and cesium carbonate (8.2 g, 25 mmol). After stirring at room temperature for 2 h, the reaction mixture was poured into ethyl acetate (100 mL) and water (100 mL). The organic layer was separated, washed with brine, dried over magnesium sulfate, filtered, and concentrated to dryness, and the residue was purified on a silica gel column eluting with 1 to 5% ethyl acetate in hexane to give the title compound. $^1$H NMR (400 MHz, CD$_3$OD): δ 7.5-6.9 (m, 9H), 3.56 (d, 1H), 3.37 (d, 1H), 2.22 (s, 3H). LC-MS: m/e 306 (M+Na)$^+$ (3.0 min).

Step B: N-[4-(4-Chlorophenyl)-3-cyano-3-phenyl-2-bulylidene]-2-methylpropane-(S)-sulfinamide.

To a solution of 4-(4-chlorophenyl)-3-cyano-3-phenyl-2-butanone (1.9 g, 6.7 mmol) and (S)-2-methysulfinamide (0.74 g, 6.1 mmol) in tetrahydrofuran (25 mL) was added titanium tetraethoxide (4.0 mL, 18 mmol). After stirring at 60° C. for 6 h and 75° C. for 18 h, the reaction mixture was poured into a well-stirred brine solution (50 mL). The resulting mixture was filtered through CELITE diatomaceous earth and washed with ethyl acetate (20 mL), and the filtrate was extracted with ethyl acetate (2×50 mL). The combined extracts were dried over anhydrous sodium sulfate, filtered, and concentrated to dryness, and the residue was purified by flash column chromatography on silica gel eluted with 10 to 20% ethyl acetate in hexane to give the title compound as a 1:1 mixture of diastereomers. LC-MS: m/e 387 (M+H)$^+$ (3.6 min).

Step C: N-{[3-(4-Chlorophenyl)-2-cyano-2-phenyl-1-methyl]propyl}-2-methylpropane-(S)-sulfinamide To a solution of N-[4-(4-chlorophenyl)-3-cyano-3-phenyl-2-butylidene]-2-methylpropane-(S)-sulfinamide (0.50 g, 1.3 mmol) in methanol (25 mL) at 0° C. was added sodium borohydride (0.075 g, 1.9 mmol). After stirring for 15 min, the reaction was quenched by addition of saturated aqueous ammonium chloride (25 mL). The organic layer was separated and the aqueous layer was extracted with ethyl acetate. The combined extracts were washed with brine, dried over anhydrous sodium sulfate, filtered and concentrated to dryness to give the title compound. LC-MS: m/e 389 (M+H)$^+$ (3.4 min).

Step D: N-{[3-(4-Chlorophenyl)-2-cyano-2-phenyl-1-methylpropyl]amine}hydrochloride salt N-{[3-(4-Chlorophenyl)-2-cyano-2-phenyl-1-methyl]propyl}-2-methylpropane-(S)-sulfinamide (0.55 g, 1.4 mmol) in methanol (20 mL) was added 4 M hydrogen chloride in dioxane (25 mL). After stirring for 30 min, the mixture was concentrated to dryness to give the title compound as a mixture of diastereomers (α and β). LC-MS: m/e 285 (M+H)$^+$ (Major diastereomer: 2.0; Minor diastereomer: 2.1 min).

REFERENCE EXAMPLE 44

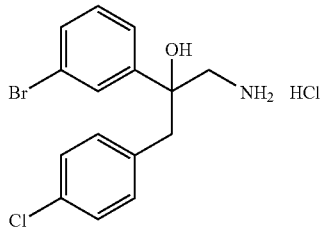

N-{[3-(4-Chlorophenyl)-2-(3-bromophenyl)-2-hydroxy]propyl}amine hydrochloride

Step A: 1-Bromo-3-{[(N-tert-butoxycarbonyl)amino]acetyl}benzene

To a solution of 1-bromo-3-iodobenzene (8.8 mL, 69 mmol) in 200 mL of ether at −78° C. was added tert-butyllithium (1.7 M in pentane, 40 mL, 69 mmol). After stirring at −78° C. for 30 min, a solution of N-(tert-butoxycarbonyl)glycine N'-methoxy-N'-methylamide (5.0 g, 23 mmol) in 100 mL of tetrahydrofuran was added. After stirring at −78° C. for 2 h, the reaction was allowed to warm up to 0° C., and was quenched with dilute aqueous ammonium chloride (200 mL). The organic layer was separated, washed with brine, dried over anhydrous magnesium sulfate, filtered, and concentrated to dryness, and the residue was purified by flash column chromatography on silica gel eluted with 5-10% ethyl acetate in hexane to give the title compound. $^1$H NMR (400 MHz, CD$_3$OD): δ 8.12 (s, 1H), 7.97 (d, 1H), 7.80 (d, 1H), 7.43 (t, 1H), 4.50 (s, 2H), 1.42 (s, 9H).

Step B: 3-(4-Chlorophenyl)-2-(3-bromophenyl)-1-[(N-butoxycarbonyl)amino-2-hydroxy]propane To a solution of 1-bromo-3-{[(N-tert-butoxycarbonyl)amino]acetyl}benzene (0.65 g, 2.1 mmol) in 25 mL of ether at −78° C. was added 4-chlorobenylmagnesium chloride (0.25 M in ether, 21 mL, 5.2 mmol). The reaction was allowed to warm up to −10° C. over 3.5 h and was quenched at −10° C. with saturated aqueous ammonium chloride (50 mL). The organic layer was separated, washed with water, dried over anhydrous magnesium sulfate, filtered, and concentrated to dryness. The residue was purified by flash column chromatography on silica gel eluted with 5-10% ethyl acetate in hexane to give the title compound. $^1$H NMR (400 MHz, CD$_3$OD): δ 7.5-7.1 (m, 4H), 7.10 (d, 2H), 6.92 (d, 2H), 3.55 (d, 2H), 3.40 (d, 2H), 3.02 (ABq, 2H), 1.38 (s, 9H).

Step C: N-{[3-(4-Chlorophenyl)-2-(3-bromophenyl)-2-hydroxy]propyl}amine hydrochloride To a solution of 3-(4-chlorophenyl)-2-(3-bromophenyl)-1-[(N-butoxycarbonyl)amino-2-hydroxy]propane (0.38 g, 0.86 mmol) in ethyl acetate (10 mL) was added 4 M hydrogen chloride in dioxane (20 mL). After stirring for 1 h, the mixture was concentrated to dryness to give the title compound. LC-MS: m/e 340 (M+H)$^+$ (2.8 min).

REFERENCE EXAMPLE 45

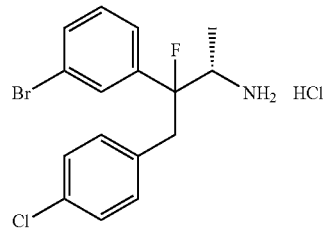

N-{[3-(4-Chlorophenyl)-2-(3-bromophenyl)-2-fluoro-1(S)-methyl]propyl}amine hydrochloride Step A: 3-(3-Bromophenyl)-2(S)-[(N-butoxycarbonyl)amino-4-(4-chlorophenyl)-3-hydroxy]butane The title compound was prepared following the same procedure described for Reference Example 44, Step A and B substituting N-(tert-butoxycarbonyl)glycine N'-methoxy-N'-methylamide with N-(tert-butoxycarbonyl)-L-alanine N'-methoxy-N'-methylamide. $^1$H NMR (500 MHz, CD$_3$OD): δ 7.5-7.0 (m, 6H), 6.82 (d, 2H), 4.11 (m, 1H), 3.07 (ABq, 2H), 1.50 (s, 9H), 0.87 (d, 3H).

Step B: 3-(3-Bromophenyl)-2(S)-[(N-butoxycarbonyl)amino-4-(4-chlorophenyl)-3-fluoro]butane To a solution of 3-(3-bromophenyl)-2(S)-[(N-butoxycarbonyl)amino-4-(4-chlorophenyl)-3-hydroxy]butane (2.0 g, 4.4 mmol) in 15 mL of methylene chloride at −78° C. was added (dimethylamino)sulfur trifluoride (1.1 mL, 8.8 mmol), and the reaction was allowed to warm up to room temperature over 2.5 h. The reaction was quenched by carefully transferring to a well-stirred saturated aqueous sodium bicarbonate (50 mL). The mixture was extracted with ether (2×50 mL), and the combined extracts were dried over anhydrous magnesium sulfate, filtered and concentrated to dryness. The residue was purified on a silica gel column eluting with 4-20% ethyl acetate in hexane to give the title compound as one major diastereomer and some contamination of the corresponding dehydration product. $^1$H NMR (500 MHz, CD$_3$OD): δ 7.4-7.1 (m, 4H), 7.06 (d, 2H), 6.85 (d, 2H), 4.19 (m, 1H), 3.43 (dd, 1H), 3.10 (dd, 1H), 1.50 (s, 9H), 0.93 (d, 3H).

Step C: N-{[3-(4-Chlorophenyl)-2-(3-bromophenyl)-2-fluoro-1(S)-methyl]propyl}amine hydrochloride To a solution of 3-(3-bromophenyl)-2(S)-[(N-butoxycarbonyl)amino-4-(4-chlorophenyl)-3-fluoro]butane (0.16 g, 0.35 mmol) in ethyl acetate (1 mL) was added 4 M hydrogen chloride in dioxane (4 mL). After stirring for 2 h, the mixture was concentrated to dryness to give the title compound. LC-MS: m/e 356 (M+H)$^+$ (3.1 min).

EXAMPLE 1

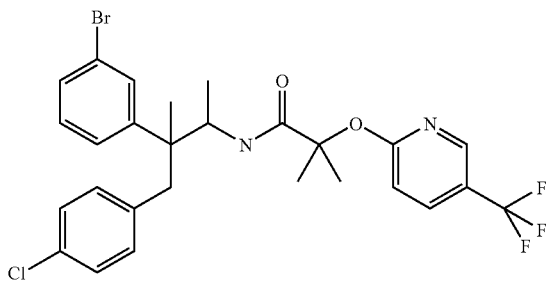

N-{[3-(4-Chlorophenyl)-2-(3-bromophenyl)-1,2-dimethyl]propyl}-2-(5-trifluoromethyl-2-pyridyloxy)-2-methylpropanamide (Diastereomer α and β)

To a solution of 2-(5-trifluoromethyl-2-pyridyloxy)-2-methylpropionic acid (Reference Example 37, 96 mg, 0.38 mmol) in methylene chloride (5 mL) was added a drop of DMF and oxalyl chloride (0.067 mL, 0.77 mmol). After stirring at room temperature overnight, the reaction mixture was concentrated on a rotary evaporator and dried under vacuum, and the resulting crude acyl chloride was used without further purification. Thus, the crude acyl chloride was suspended in 3 mL of methylene chloride and was added to a suspension of N-{[2-(3-bromophenyl)-3-(4-chlorophenyl)-1,2-dimethyl]propyl}amine hydrcloride (Reference Example 42, Diastereomer α, 0.10 g, 0.26 mmol) and N-methylmorpholine (0.17 mL, 1.5 mmol) in 3 mL of methylene chloride. After stirring at room temperature for 6 h, the reaction mixture was loaded onto a silica gel column, which was eluted with 10% ethyl acetate to give a pure faster eluting isomer of the title compound (diastereomer α). $^1$H NMR (400 MHz, CD$_3$OD): δ 8.38 (br s, 1H), 8.02 (dd, 1H), 7.57 (d, 1H), 7.4-7.0 (m, 4H), 6.98 (d, 2H), 6.42 (d, 2H), 4.60 (m, 1H), 3.03 (d, 1H), 2.73 (d, 1H), 1.80 (s, 3H), 1.72 (s, 3H), 0.90 (s, 3H), 0.74 (d, 3H). LC-MS: m/e 583 (M+H)$^+$ (4.3 min).

Diastereomer β of the title compound was prepared following the same procedure as described for Diastereomer α substituting Diastereomer α of N-{[2-(3-bromophenyl)-3-(4-chlorophenyl)-1,2-dimethyl]propyl}amine hydrochloride with Diastereomer β of N-{[2-(3-bromophenyl)-3-(4-chlorophenyl)-1,2-dimethyl]propyl}amine hydrochloride. $^1$H NMR (400 MHz, CD$_3$OD): δ 8.28 (br s, 1H), 8.00 (dd, 1H), 7.4-6.9 (m, 7H), 6.70 (d, 2H), 4.38 (m, 1H), 3.19 (d, 1H), 2.83 (d, 1H), 1.57 (s, 3H), 1.46 (s, 3H), 1.20 (s, 3H), 1.00 (d, 3H). LC-MS: m/e 583 (M+H)$^+$ (4.4 min).

EXAMPLE 2

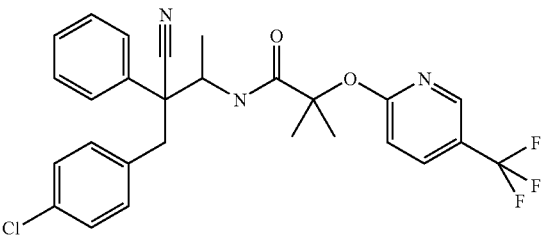

N-{[3-(4-Chlorophenyl)-2-cyano-2-phenyl-1-methyl]propyl}-2-(5-trifluoromethyl-2-pyridyloxy-2-methylpropanamide (Enantiomers A, B, C, D)

To a mixture of N-{[3-(4-chlorophenyl)-2-phenyl-2-cyano-1-methyl]propyl}amine hydrochloride (Reference Example 43, 0.20 g, 0.62 mmol) and 2-(5-trifluoromethyl-2-pyridyloxy)-2-methylpropionic acid (Reference Example 37, 0.23 g, 0.93 mmol) in 5 mL methylene chloride was added N-methylmorpholine (0.41 mL, 3.7 mmol) and tris(pyrrolindinyl)phosphonium hexafluorophosphate (0.49 g, 0.93 mmol). After stirring at room temperature for 1 h, the reaction mixture was loaded onto a silica gel column eluted with 10-15% ethyl acetate in hexane to give the title compound as one major diastereomer and a mixture of the two diastereomers.

The mixture of diastereomers was then separated into four stereoisomers by preparative HPLC, eluting on a Chiralpak AD-H column (2 cm×25 cm) with 8% ethanol in hexane (flow rate 12 mL/min).

Enantiomer A: Analytical HPLC: retention time=7.8 min (Chiralpak AD column, flow rate=0.75 mL/min, 8% ethanol/hexane). $^1$H NMR (400 MHz, CD$_3$OD): δ 8.36 (br s, 1H), 8.02 (dd, 1H), 7.4-7.2 (m, 4H), 7.11 (d, 1H), 7.00 (d, 2H), 6.63 (d, 2H), 4.77 (q, 1H), 3.42 (d, 1H), 3.21 (d, 1H), 1.82 (s, 3H), 1.78 (s, 3H), 0.96 (d, 3H).

Enantiomer B: Analytical HPLC: retention time=9.0 min (Chiralpak AD column, flow rate=0.75 mL/min, 8% ethanol/hexane). $^1$H NMR (400 MHz, CD$_3$OD): δ 8.36 (br s, 1H), 8.02 (dd, 1H), 7.3-7.0 (m, 6H), 7.00 (d, 1H), 6.83 (d, 2H), 4.80 (q, 1H), 3.33 (ABq 2H), 1.56 (s, 3H), 1.42 (s, 3H), 1.24 (d, 3H).

Enantiomer C: Analytical HPLC: retention time=10.1 min (Chiralpak AD column, flow rate=0.75 mL/min, 8% ethanol/hexane). $^1$H NMR (400 MHz, CD$_3$OD): δ 8.36 (br s, 1H), 8.03 (dd, 1H), 7.4-7.1 (m, 5H), 7.00 (d, 2H), 6.64 (d, 2H), 4.78 (q, 1H), 3.42 (d, 1H), 3.22 (d, 1H), 1.82 (s, 3H), 1.78 (s, 3H), 0.95 (d, 3H).

Enantiomer D: Analytical HPLC: retention time=10.4 min (Chiralpak AD column, flow rate=0.75 mL/min, 8% ethanol/hexane). $^1$H NMR (400 MHz, CD$_3$OD): δ 8.36 (br s, 1H), 8.02 (dd, 1H), 7.3-7.0 (m, 6H), 7.00 (d, 1H), 6.84 (d, 2H), 4.79 (q, 1H), 3.33 (ABq 2H), 1.57 (s, 3H), 1.43 (s, 3H), 1.24 (d, 3H).

EXAMPLE 3

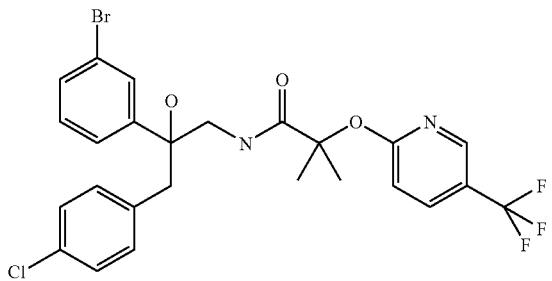

N-{[3-(4-Chlorophenyl)-2-(3-bromophenyl)-2-hydroxy]propyl}-2-(5-trifluoromethyl-2-pyridyloxy)-2-methylpropanamide To a mixture of N-{[3-(4-chlorophenyl)-2-(3-bromophenyl)-2-hydroxy]propyl}amine hydrochloride (Reference Example 44, 0.35 g, 0.93 mmol) and 2-(5-trifluoromethyl-2-pyridyloxy)-2-methylpropionic acid (Reference Example 37, 0.35 g, 1.4 mmol) in 5 mL of methylene chloride was added N-methylmorpholine (0.62 mL, 5.6 mmol) and tris(pyrrolindinyl)phosphonium hexafluorophosphate (0.73 g, 1.4 mmol). After stirring at room temperature overnight, the reaction mixture was loaded onto a silica gel column eluted with 15-20% ethyl acetate in hexane to give the title compound. $^1$H NMR (400 MHz, CD$_3$OD): δ 8.24 (br s, 1H), 7.92 (dd, 1H), 7.42 (s, 1H), 7.30 (d, 1H), 7.20 (d, 1H), 7.15-7.05 (m, 3H), 7.92-7.85 (m, 3H), 3.76 (d, 2H), 3.42 (d, 2H), 2.98 (ABq, 2H), 1.57 (s, 3H), 1.48 (s, 3H). LC-MS: m/e 593 (M+Na)$^+$ (4.3 min).

EXAMPLE 4

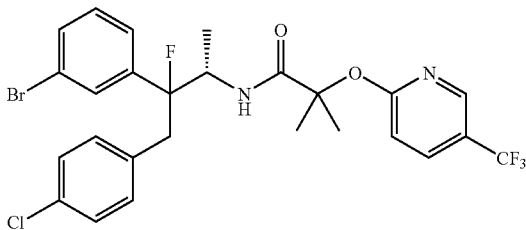

N-{[3-(4-Chlorophenyl)-2-(3-bromophenyl)-2-fluoro-1(S)-methyl]propyl}-2-(5-trifluoromethyl-2-pyridyloxy)-2-methylpropanamide To a solution of 2-(5-trifluoromethyl-2-pyridyloxy)-2-methylpropionic acid (Reference Example 37, 0.13 mg, 0.53 mmol) in toluene (2 mL) was added thionyl chloride (0.077 mL, 1.1 mmol). After stirring at 50° C. for 1 h, the reaction mixture was concentrated on a rotary evaporator and dried under vacuum, and the resulting crude acyl chloride was used without further purification. Thus, the crude acyl chloride was suspended in 3 mL of acetonitrile and was added to a suspension of N-{[3-(4-chlorophenyl)-2-(3-bromophenyl)-2-fluoro-1(S)-methyl]propyl}amine hydrochloride (Reference Example 45, 0.15 g, 0.35 mmol) and triethyl amine (0.10 mL, 1.4 mmol) in 3 mL of acetonitrile. After stirring at room temperature for 2 h, the reaction mixture was diluted with ethyl acetate (100 mL), washed with dilute aqueous sodium hydroxide, brine, dried over anhydrous magnesium sulfate, filtered and concentrated to dryness. The residue was purified on a silica gel column eluting with 4-25% ethyl acetate in hexane to give the title compound as one major diastereomer along with some dehydration product. $^1$H NMR (500 MHz, CD$_3$OD): δ 8.27 (d, 1H), 7.98 (dd, 1H), 7.37 (br d, 1H), 7.28 (br s, 1H), 7.20 (t, 1H), 7.13 (d, 1H), 7.08 (d, 1H), 7.02 (d, 2H), 6.66 (d, 2H), 4.58 (m, 1H), 3.33 (dd, 1H), 2.98 (dd, 1H), 1.80 (s, 3H), 0.85 (d, 3H). LC-MS: m/e 587 (M+H)$^+$ (4.4 min).

EXAMPLE 5

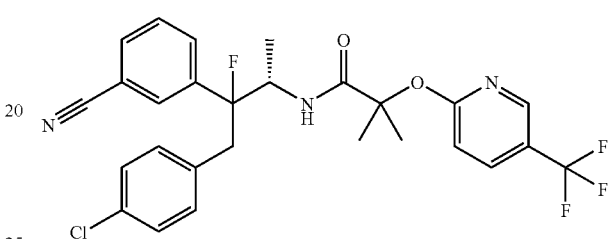

N-{[3-(4-Chlorophenyl)-2-(3-cyanophenyl)-2-fluoro-1(S)-methyl]propyl}-2-(5-trifluoromethyl-2-pyridyloxy)-2-methylpropanamide A mixture of N-{[3-(4-chlorophenyl)-2-(3-bromophenyl)-2-fluoro-1(S)-methyl]propyl}-2-(5-trifluoromethyl-2-pyridyloxy)-2-methylpropanamide (Example 4, 0.12 g, 0.22 mmol), sodium cyanide (0.015 g, 0.31 mmol), 18-crown-6 (63 mg, 0.32 mmol) and tetrakis(triphenylphosphine)palladium (50 mg, 0.04 mmol) in 2 mL of dioxane was heated under nitrogen at 100° C. for 5 h. After cooling to room temperature, the volatile materials were removed under vacuum, and the residue was purified by flash column chromatography on silica gel eluting with 5 to 50% ethyl acetate in hexane to afford the title compound as one major diastereomer along with trace amount of the dehydration product. $^1$H NMR (500 MHz, CD$_3$OD): δ 8.26 (d, 1H), 7.98 (dd, 1H), 7.58 (m, 1H), 7.52-7.44 (m, 2H), 7.08 (d, 1H), 7.02 (d, 1H), 7.01 (d, 1H), 6.67 (d, 2H), 4.63 (m, 1H), 3.38 (dd, 1H), 3.03 (dd, 1H), 1.80 (s, 3H), 1.76 (s, 3H), 0.84 (d, 3H). LC-MS: m/e 534 (M+H)$^+$ (4.2 min).

EXAMPLE 6

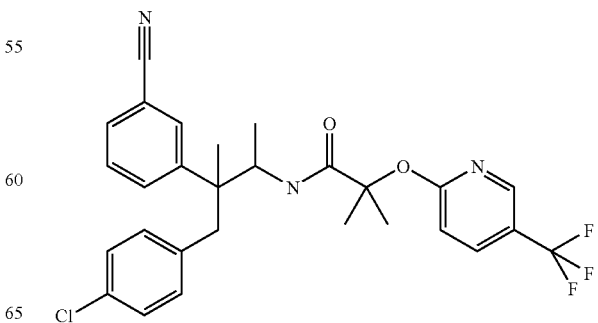

N-{[3-(4-Chlorophenyl)-2-(3-cyanophenyl)-1,2-dimethyl]propyl}2-(5-trifluoromethyl-2-pyridyloxy)-2-methylpropanamide (Diastereomer α)

The title compound was prepared following the same procedure as described in Example 5 substituting N-{[3-(4-chlorophenyl)-2-(3-bromophenyl)-2-fluoro-1(S)-methyl]propyl}-2-(5-trifluoromethyl-2-pyridyloxy)-2-methylpropanamide with N-{[3-(4-chlorophenyl)-2-(3-cyanophenyl)-1,2-dimethyl]propyl}-2-(5-trifluoromethyl-2-pyridyloxy)-2-methylpropanamide (Example 1, Diastereomer α). $^1$H NMR (400 MHz, CD$_3$OD): δ 8.37 (br s, 1H), 8.03 (dd, 1H), 7.66-7.46 (m, 4H), 7.09 (d, 1H), 6.98 (d, 1H), 6.42 (d, 2H), 4.63 (q, 1H), 3.07 (d, 1H), 2.79 (d, 1H), 1.80 (s, 3H), 1.76 (s, 3H), 0.99 (s, 3H), 0.72 (d, 3H). LC-MS: m/e 552 (M+Na)$^+$ (4.2 min).

EXAMPLE 7

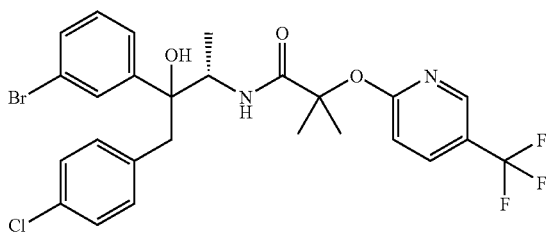

N-{[3-(4-Chlorophenyl)-2-(3-bromophenyl)-2-hydroxy-1(S)-methyl]propyl}-2-(5-trifluoromethyl-2-pyridyloxy)-2-methylpropanamide (Diastereomer α and β)

Step A: N-{[2-(5-Trifluoromethyl-2-pyridyloxy)-2-methyl]propionyl-L-alanine Methyl Ester.
To a mixture of L-alanine methyl ester (Aldrich, 5.0 g, 36 mmol) and 2-(5-trifluoromethyl-2-pyridyloxy)-2-methylpropionic acid (Reference Example 37, 6.3 g, 25 mmol) in 100 mL of methylene chloride was added N-methylmorpholine (14 mL, 0.10 mol) and tris(pyrrolindinyl)phosphonium hexafluorophosphate (20 g, 38 mmol). After stirring at room temperature for 4 h, the reaction mixture was diluted with ether (300 mL), washed with dilute aqueous sodium hydroxide, dried over sodium sulfate, filtered and concentrated to dryness. The residue loaded onto a silica gel column eluted with 15-20% ethyl acetate in hexane to give the title compound. $^1$H NMR (400 MHz, CD$_3$OD): δ 8.38 (d, 1H), 7.94 (dd, 1H), 6.99 (d, 1H), 4.42 (q, 1H), 3.64 (s, 3H), 1.71 (s, 3H), 1.69 (s, 3H), 1.27 (d, 3H).

Step B: N-{[2-(5-Trifluoromethyl-2-pyridyloxy)-2-methyl]propionyl-L-alanine N'-methoxy-N'-methylamide
To a suspension of N-methoxy-N-methylamine hydrochloride (4.4 g, 45 mmol) in 100 mL of methylene chloride at 0° C. was added dimethylaluminum chloride (4.0 mL, 45 mmol). After stirring at room temperature for 10 min, a solution of N-{[2-(5-trifluoromethyl-2-pyridyloxy)-2-methyl]propionyl-L-alanine methyl ester (7.0 g, 21 mmol) in methylene chloride (100 mL) was added, and the resulting mixture was stirred for 2 h. The reaction mixture was quenched by pouring into a stirred mixture of 2 M hydrochloric acid (200 mL) and ice (200 g). The organic layer was separated and the aqueous layer extracted with ether (2×100 m)). The combined extracts were washed with 2 M hydrochloric acid, dilute aqueous sodium hydroxide, water nd brine, dried over anhydrous magnesium sulfate, filtered and concentrated to dryness to give the title compound, which was used without further purification.

Step C: N-[1(S)-(3-Bromobenzoyl)ethyl]-2-(6-trifluoromethyl-2-pyridyloxy)-2-methylpropanamide To a solution of 1-bromo-3-iodobenzene (7.7 mL, 60 mmol) in 100 mL of ether at −78° C. was added tert-butyllithium (1.7 M in pentane, 35 mL, 60 mmol). After stirring at −78° C. for 15 min, a solution of N-{[2-(5-trifluoromethyl-2-pyridyloxy)-2-methyl]propionyl-L-alanine N'-methoxy-N'-methylamide (7.7 g, 21 mmol) in 50 mL of ether was added. After stirring at −78° C. for 30 min, the reaction was quenched with saturated aqueous ammonium chloride (20 mL), and was allowed to warm up to room temperature. The reaction mixture was partitioned between saturated ammonium chloride (200 mL) and ether/hexane (1:1, 200 mL). The organic layer was separated, washed with water and brine, dried over anhydrous magnesium sulfate, filtered, and concentrated to dryness, and the residue was purified by flash column chromatography on silica gel eluted with 0-60% ether in hexane to give the title compound. $^1$H NMR (500 MHz, CD$_3$OD): δ 8.2-6.9 (m. 7H), 5.28 (q, 1H), 1.63 (s, 3H), 1.62 (s, 3H), 1.27 (d, 3H).

Step D: N-{[3-(4-Chlorophenyl)-2-(3-bromophenyl)-2-hydroxy-1(S)-methyl]propyl}-2-(5-trifluoromethyl-2-pyridyloxy)-2-methyl-propanamide (Diastereomers α and β)

To a solution of N-[1(S)-(3-bromobenzoyl)ethyl]-2-(6-trifluoromethyl-2-pyridyloxy)-2-methylpropanamide (6.6 g, 14 mmol) in 50 mL of ether at −10° C. was added 4-chlorobenylmagnesium chloride (0.25 M in ether, 125 mL, 31 mmol). The reaction was allowed to warm up to 0° C. over 2 h and was quenched by pouring into saturated aqueous ammonium chloride (200 mL). The organic layer was separated and the aqueous layer extracted with ethyl acetate 100 mL). The combined organic extracts were dried over anhydrous magnesium sulfate, filtered, and concentrated to dryness. The residue was purified by flash column chromatography on silica gel eluted with 0-50% ethyl acetate in hexane to give the title compound as a faster eluting diastereomer (Diastereomer α, after recrystallization from tert-butyl methyl ether and hexane) and a slower eluting diastereomer (Diastereomer β) and mixed fractions containing both diastereomers and recovered starting material.

Diastereomer α: $^1$H NMR (500 MHz, CD$_3$OD): δ 8.34 (d, 1H), 8.00 (dd, 1H), 7.38 (m, 1H), 7.34 (m, 1H), 7.22-7.16 (m, 2H), 7.08 (d, 1H), 7.03 (d, 2H), 6.68 (d, 2H), 4.46 (q, 1H), 2.91 (ABq, 2H), 1.82 (s, 3H), 1.78 (s, 3H), 0.80 (d, 3H). LC-MS: m/e 585 (M+H)$^+$ (4.4 min).

Diastereomer β: $^1$H NMR (500 MHz, CD$_3$OD): δ 8.30 (d, 1H), 7.33 (dd, 1H), 7.26 (ddd, 1H), 7.12 (ddd, 1H), 7.09-7.02

(m, 3H), 6.92 (d, 1H), 6.82 (d, 2H), 4.46 (q, 1H), 3.07 (ABq, 2H), 1.49 (s, 3H), 1.28 (s, 3H), 1.24 (d, 3H). LC-MS: m/e 585 (M+H)$^+$ (4.4 min).

EXAMPLE 8

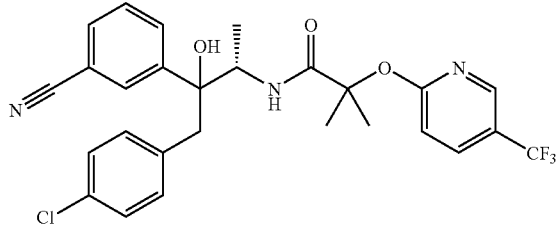

N-{[3-(4-Chlorophenyl)-2-(3-cyanophenyl)-2-hydroxy-1(S)-methyl]propyl}-2-(5-trifluoromethyl-2-pyridyloxy)-2-methylpropanamide (Diastereomer α)

A mixture of N-{[3-(4-chlorophenyl)-2-(3-bromophenyl)-2-hydroxy-1(S)-methyl]propyl}-2-(5-trifluoromethyl-2-pyridyloxy)-2-methylpropanamide (Diastereomer α, Example 7, 1.8 g, 3.1 mmol), sodium cyanide (0.23 g, 4.6 mmol), 18-crown-6 (1.2 g, 4.6 mmol) and tetrakis(triphenylphosphine)palladium (1.8 g, 1.6 mmol) in 50 mL of dioxane was heated under nitrogen at 100° C. for 4 h. After cooling to room temperature, the reaction mixture was partitioned between ether (200 mL) and water (200 mL). The organic layer was separated and the aqueous layer extracted with ether (200 mL). The combined extracts were dried over anhydrous magnesium sulfate, filtered, and concentrated to dryness. The residue was purified by flash column chromatography on silica gel eluting with 5 to 20% ethyl acetate in hexane/methylene chloride (1:1) to afford the title compound after recrystallization from ethyl acetate/hexane. Analytically pure sample was prepared by reverse-phase HPLC eluting with 50-100% acetonitrile in water (0.1% trifluoroacetic acid in each solvent) and recrystallization from ethyl acetate and hexane. $^1$H NMR (500 MHz, CD$_3$OD): δ 8.32 (br s, 1H), 7.98 (dd, 1H), 7.58-7.41 (m, 3H), 7.42 (dd, 1H), 7.07 (d, 1H), 7.02 (d, 2H), 6.68 (d, 2H), 4.49 (q, 1H), 2.94 (ABq, 2H), 1.80 (s, 3H), 1.77 (s, 3H), 0.78 (d, 3H). LC-MS: m/e 532 (M+H)$^+$ (4.0 min).

EXAMPLE 9

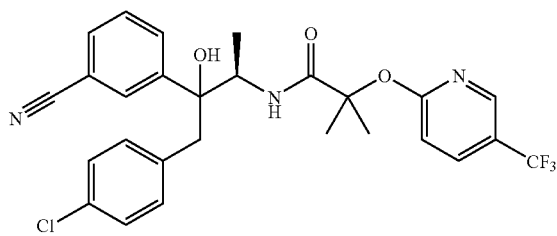

N-{[3-(4-Chlorophenyl)-2-(3-cyanophenyl)-2-hydroxy-1(R)-methyl]propyl}-2-(5-trifluoromethyl-2-pyridyloxy)-2-methylpropanamide The title compound was prepared following the procedure as described in Example 8 starting form D-alanine methyl ester. LC-MS: m/e 532 (M+H)$^+$ (4.0 min).

BIOLOGICAL EXAMPLE 1

Cannabinoid Receptor-1 (CB1) Binding Assay.

Binding affinity determination is based on recombinant human CB1 receptor expressed in Chinese Hamster Ovary (CHO) cells (Felder et al, Mol. Pharmacol. 48: 443-450, 1995). Total assay volume is 250 µl (240 µl CB1 receptor membrane solution plus 5 µl test compound solution plus 5 µl [3H]CP-55940 solution). Final concentration of [3H]CP-55940 is 0.6 nM. Binding buffer contains 50 mM Tris-HCl, pH7.4, 2.5 mM EDTA, 5 mM MgCl2, 0.5mg/mL fatty acid free bovine serum albumin and protease inhibitors (Cat#P8340, from Sigma). To initiate the binding reaction, 5 µl of radioligand solution is added, the mixture is incubated with gentle shaking on a shaker for 1.5 h at 30° C. The binding is terminated by using 96-well harvester and filtering through GF/C filter presoaked in 0.05% polyethylenimine. The bound radiolabel is quantitated using scintillation counter. Apparent binding affinities for various compounds are calculated from IC50 values (DeBlasi et al., Trends Pharmacol Sci 10: 227-229, 1989).

The binding assay for CB2 receptor is done similarly with recombinant human CB2 receptor expressed in CHO cells.

BIOLOGICAL EXAMPLE 2

Cannabinoid Receptor-1 (CB1) Functional Activity Assay.

The functional activation of CB1 receptor is based on recombinant human CB1 receptor expressed in CHO cells (Felder et al, Mol. Pharmacol. 48: 443-450, 1995). To determine the agonist activity or inverse agonist activity of any test compound, 50 ul of CB1-CHO cell suspension are mixed with test compound and 70 ul assay buffer containing 0.34 mM 3-isobutyl-1-methylxanthine and 5.1 uM of forskolin in 96-well plates. The assay buffer is comprised of Earle's Balanced Salt Solution supplemented with 5 mM MgCl2, 1 mM glutamine, 10 mM HEPES, and 1 mg/mL bovine serum albumin. The mixture is incubated at room temperature for 30 minutes, and terminated by adding 30 ul/well of 0.5M HCl. The total intracellular cAMP level is quantitated using the New England Nuclear Flashplate and cAMP radioimmunoassay kit.

To determine the antagonist activity of test compound, the reaction mixture also contains 0.5 nM of the agonist CP55940, and the reversal of the CP55940 effect is quantitated. Alternatively, a series of dose response curves for CP55940 is performed with increasing concentration of the test compound in each of the dose response curves.

The functional assay for the CB2 receptor is done similarly with recombinant human CB2 receptor expressed in CHO cells.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

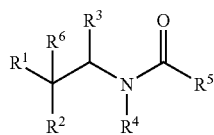

(I)

or a pharmaceutically acceptable salt thereof, wherein;
$R^1$ is selected from:
  (1) aryl,
  (2) aryl-$C_{1-4}$alkyl,
  (3) heteroaryl,
  (4) heteroaryl-$C_{1-4}$alkyl,
  wherein each alkyl is optionally substituted with one to four substituents independently selected from $R^a$, and each aryl and heteroaryl are optionally substituted with one to four substituents independently selected from $R^b$;
$R^2$ is benzyl, unsubstituted or substituted with halogen, cyano, trifluoromethyl or methoxy;
$R^3$ is selected from:
  (1) hydrogen, and
  (2) $C_{1-4}$alkyl,
  wherein each alkyl is optionally substituted with one to four substituents independently selected from $R^a$;
$R^4$ is selected from:
  (1) hydrogen, and
  (2) $C_{1-4}$alkyl,
  wherein each alkyl is optionally substituted with one to four substituents independently selected from $R^a$;
$R^5$ is selected from:
  (1) $C_{1-8}$alkyl substituted with —$OR^d$ or $NR^cR^d$,
  (2) $C_{2-8}$alkenyl substituted with $OR^d$ or $NR^cR^d$, and
  (3) phenyl-$C_{1-8}$alkyl wherein phenyl is substituted with one to three $R^b$ substitutents;
$R^6$ is selected from:
  (1) $C_{1-4}$alkyl,
  (2) $C_{2-4}$alkenyl,
  (3) $C_{2-4}$alkynyl,
  (4) halogen, and
  (5) —CN,
  wherein alkyl, alkenyl, and alkynyl are optionally substituted with one to four substituents independently selected from $R^a$;
each $R^a$ is independently selected from:
  (1) —$OR^d$,
  (2) —$NR^cS(O)_mR^d$,
  (3) halogen,
  (4) —$S(O)_mR^d$,
  (5) —$S(O)_mNR^cR^d$,
  (6) —$NR^cR^d$,
  (7) —$C(O)R^d$,
  (8) —$CO_2R^d$,
  (9) —CN,
  (10) —$C(O)NR^cR^d$,
  (11) —$NR^cC(O)R^d$,
  (12) —$NR^cC(O)OR^d$,
  (13) —$NR^cC(O)NR^cR^d$,
  (14) —$CF_3$,
  (15) —$OCF_3$, and
  (16) cycloheteroalkyl;
each $R^b$ is independently selected from:
  (1) $R^a$,
  (2) $C_{1-10}$alkyl,
  (3) oxo,
  (4) aryl,
  (5) aryl$C_{1-4}$alkyl,
  (6) heteroaryl, and
  (7) heteroaryl$C_{1-4}$alkyl;
$R^c$ and $R^d$ are independently selected from:
  (1) hydrogen,
  (2) $C_{1-10}$alkyl,
  (3) $C_{2-10}$alkenyl,
  (4) cycloalkyl,
  (5) cycloalkyl-$C_{1-10}$alkyl;
  (6) cycloheteroalkyl,
  (7) cycloheteroalkyl-$C_{1-10}$alkyl;
  (8) aryl,
  (9) heteroaryl,
  (10) aryl-$C_{1-10}$alkyl, and
  (11) heteroaryl-$C_{1-10}$alkyl, or
$R^c$ and $R^d$ together with the atom(s) to which they are attached form a heterocyclic ring of 4 to 7 members containing 0-2 additional heteroatoms independently selected from oxygen, sulfur and N—$R^g$,
each $R^c$ and $R^d$ may be unsubstituted or substituted with one to three substituents selected from $R^h$;
each $R^g$ is independently selected from: $C_{1-10}$alkyl, and —$C(O)R^c$;
each $R^h$ is independently selected from:
  (1) halogen,
  (2) $C_{1-10}$alkyl,
  (3) —O $C_{1-4}$alkyl,
  (4) —S $(O)_m$ $C_{1-4}$alkyl,
  (5) —CN,
  (6) —$CF_3$, and
  (7) —$OCF_3$; and
m is selected from 0, 1 and 2.

2. The compound according to claim 1, wherein $R^4$ is selected from:
  (1) hydrogen, and
  (2) methyl;
and pharmaceutically acceptable salts thereof.

3. The compound according to claim 2, wherein $R^4$ is hydrogen;
and pharmaceutically acceptable salts thereof.

4. The compound according to claim 2, wherein $R^3$ is selected from hydrogen, methyl and ethyl; and pharmaceutically acceptable salts thereof.

5. The compound according to claim 3, wherein $R^3$ is methyl; and pharmaceutically acceptable salts thereof.

6. The compound according to claim 4, wherein $R^1$ is selected from:
  (1) phenyl,
  (2) phenyl-$C_{1-4}$alkyl,
  (3) pyridyl, and (4) pyridyl-$C_{1-4}$alkyl,
wherein each phenyl and pyridyl is optionally substituted with one or two substituents selected from halogen, methyl, trifluoromethyl, cyano and methoxy, and each pyridyl is optionally present as the N-oxide;
and pharmaceutically acceptable salts thereof.

7. The compound according to claim 5, wherein $R^1$ is phenyl, unsubstituted or substituted with a halogen or cyano substituent; and pharmaceutically acceptable salts thereof.

8. The compound according to claim 7, wherein $R^2$ is 4-chlorobenzyl, and pharmaceutically acceptable salts thereof.

9. The compound according to claim 8, wherein $R^6$ is selected from:
  (1) methyl,
  (2) halogen, and
  (3) —CN;
and pharmaceutically acceptable salts thereof.

10. The compound according to claim 1, wherein $R^5$ is:

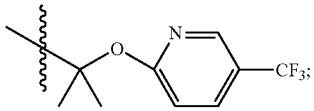

and pharmaceutically acceptable salts thereof.

11. The compound according to claim 1, selected from:
  (1) N-{[3-(4-chlorophenyl)-2-(3-bromophenyl)-1,2-dimethyl]propyl}-2-(5-trifluoromethyl-2-pyridyloxy)-2-methylpropanamide,
  (2) N-{[3-(4-chlorophenyl)-2-cyano-2-phenyl-1-methyl]propyl}-2-(5-trifluoromethyl-2pyridyloxy)-2-methylpropanamide,
  (3) N-{[3-(4-chlorophenyl)-2-(3-bromophenyl)-2-fluoro-1(S)-methyl]propyl}-2-(5-trifluoromethyl-2-pyridyloxy)-2-methylpropanamide,
  (4) N-{[3-(4-chlorophenyl)-2-(3-cyanophenyl)-2-fluoro-1(S)-methyl]propyl}-2-(5-triflouromethyl-2-pyridyloxy)-2-methylpropanamide,
  (5) N-{[3-(4-chlorophenyl)-2-(3-cyanophenyl)-1,2-dimethyl]propyl}-2-(5-trifluoromethyl-2-pyridyloxy)-2-methylpropanamide,
  (6) 1-{[3-(4-chlorophenyl)-2-(3-cyanophenyl)-2-fluoro-1(S)-methyl]propyl}-3-[2-(phenyl)ethyl]urea, and
  (7) N-{[3-(4-chlorophenyl)-2-(3-cyanophenyl)-2-fluoro-1(S)-methyl]propyl}-1-ethyl-cyclobutanecarboxamide,
and pharmaceutically acceptable salts thereof.

12. A composition comprising a compound according to claim 1 and a pharmaceutically acceptable carrier.

* * * * *